United States Patent
Cao et al.

(10) Patent No.: US 11,289,300 B2
(45) Date of Patent: Mar. 29, 2022

(54) INTEGRATED X-RAY SOURCE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 31 days.

(21) Appl. No.: 16/742,733

(22) Filed: Jan. 14, 2020

(65) Prior Publication Data
US 2020/0161075 A1    May 21, 2020

Related U.S. Application Data

(63) Continuation of application No. PCT/CN2017/094442, filed on Jul. 26, 2017.

(51) Int. Cl.
| | |
|---|---|
| H01J 35/06 | (2006.01) |
| H01J 35/08 | (2006.01) |
| A61B 6/00 | (2006.01) |
| H01J 35/04 | (2006.01) |
| A61B 6/03 | (2006.01) |

(52) U.S. Cl.
CPC .......... H01J 35/065 (2013.01); A61B 6/4007 (2013.01); H01J 35/045 (2013.01); H01J 35/116 (2019.05); A61B 6/032 (2013.01); H01J 2235/02 (2013.01); H01J 2235/062 (2013.01)

(58) Field of Classification Search
CPC .. H01J 35/065; H01J 2235/062; H01J 35/045; H01J 35/116
See application file for complete search history.

(56) References Cited

U.S. PATENT DOCUMENTS

| | | | | |
|---|---|---|---|---|
| 3,882,339 A | * | 5/1975 | Rate, Jr. | H01J 35/26 378/124 |
| 4,982,096 A | * | 1/1991 | Fujii | G01T 1/2018 250/366 |
| 5,144,191 A | * | 9/1992 | Jones | H01J 3/022 313/308 |
| 5,721,759 A | * | 2/1998 | Raatikainen | G01N 23/223 378/47 |
| 5,973,444 A | * | 10/1999 | Xu | H01J 1/304 313/309 |
| 5,975,975 A | | 11/1999 | Hofmann et al. | |
| 8,588,372 B2 | | 11/2013 | Zou et al. | |
| 8,897,419 B1 | * | 11/2014 | Jacob | H01J 35/04 378/126 |

(Continued)

FOREIGN PATENT DOCUMENTS

| | | |
|---|---|---|
| CN | 101101848 A | 1/2008 |
| CN | 102224560 A | 10/2011 |

(Continued)

*Primary Examiner* — Chih-Cheng Kao
(74) *Attorney, Agent, or Firm* — IPRO, PLLC

(57) ABSTRACT

Disclosed herein is an X-ray source, comprising: a cathode in a recess of a first substrate; a counter electrode on a sidewall of the recess, configured to cause field emission of electrons from the cathode; and a metal anode configured to receive the electrons emitted from the cathode and to emit X-ray from impact by the electrons on the metal anode.

26 Claims, 33 Drawing Sheets

(56) References Cited

U.S. PATENT DOCUMENTS

| | | | |
|---|---|---|---|
| 2004/0001571 A1* | 1/2004 | Jahrling | A61B 6/0487 378/209 |
| 2004/0240616 A1 | 12/2004 | Qiu et al. | |
| 2006/0039532 A1* | 2/2006 | Wu | A61B 6/484 378/62 |
| 2007/0189459 A1* | 8/2007 | Eaton | H01J 35/065 378/143 |
| 2008/0187093 A1 | 8/2008 | Price et al. | |
| 2009/0052615 A1* | 2/2009 | Ribbing | A61B 6/032 378/9 |
| 2009/0141860 A1* | 6/2009 | Ryge | G01T 1/2008 378/62 |
| 2010/0200757 A1* | 8/2010 | Sarin | C23C 16/40 250/361 R |
| 2011/0142193 A1 | 6/2011 | Frontera et al. | |
| 2012/0300904 A1* | 11/2012 | Shimada | A61B 6/542 378/62 |
| 2013/0214244 A1 | 8/2013 | Sanborn et al. | |
| 2013/0230147 A1* | 9/2013 | Matsumoto | H01J 35/066 378/140 |
| 2014/0124679 A1* | 5/2014 | Unfors | G01T 1/02 250/395 |

FOREIGN PATENT DOCUMENTS

| | | | |
|---|---|---|---|
| CN | 102347186 A | 2/2012 | |
| CN | 102420088 A | 4/2012 | |
| CN | 103250225 A | 8/2013 | |
| CN | 104411081 A | 3/2015 | |
| JP | 11307031 A * | 11/1999 | |
| JP | 2009087633 A | 4/2009 | |
| WO | WO-2007135813 A1 * | 11/2007 | H01J 35/18 |

* cited by examiner

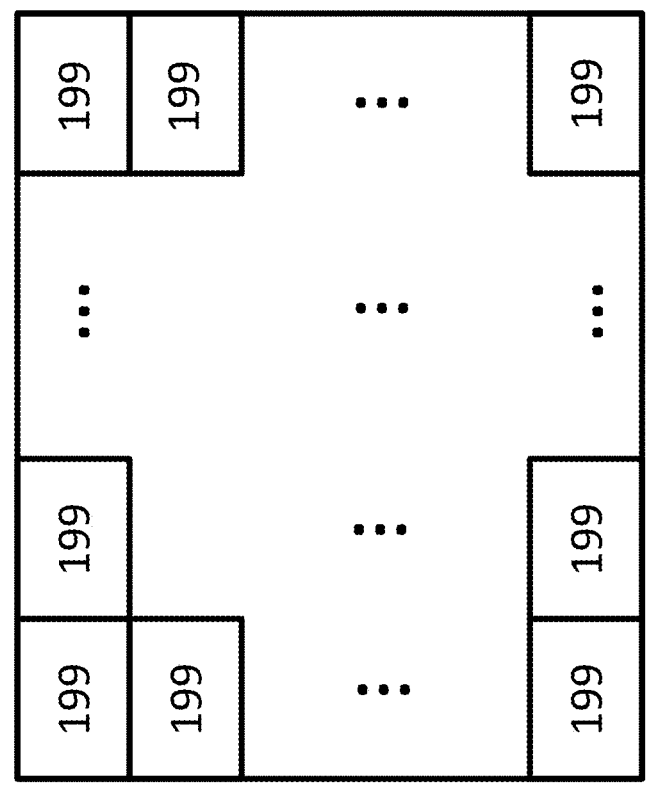
Fig. 3B

INTEGRATED X-RAY SOURCE

TECHNICAL FIELD

The disclosure herein relates to an X-ray source integrated on a chip.

BACKGROUND

X-ray fluorescence (XRF) is the emission of characteristic fluorescent X-rays from a material that has been excited by, for example, exposure to high-energy X-rays or gamma rays. An electron on an inner orbital of an atom may be ejected, leaving a vacancy on the inner orbital, if the atom is exposed to X-rays or gamma rays with photon energy greater than the ionization potential of the electron. When an electron on an outer orbital of the atom relaxes to fill the vacancy on the inner orbital, an X-ray (fluorescent X-ray or secondary X-ray) is emitted. The emitted X-ray has a photon energy equal the energy difference between the outer orbital and inner orbital electrons.

For a given atom, the number of possible relaxations is limited. As shown in FIG. 1A, when an electron on the L orbital relaxes to fill a vacancy on the K orbital (L→K), the fluorescent X-ray is called Kα. The fluorescent X-ray from M→K relaxation is called Kβ. As shown in FIG. 1B, the fluorescent X-ray from M→L relaxation is called La, and so on.

Analyzing the fluorescent X-ray spectrum can identify the elements in a sample because each element has orbitals of characteristic energy. The fluorescent X-ray can be analyzed either by sorting the energies of the photons (energy-dispersive analysis) or by separating the wavelengths of the fluorescent X-ray (wavelength-dispersive analysis). The intensity of each characteristic energy peak is directly related to the amount of each element in the sample.

Proportional counters or various types of solid-state detectors (PIN diode, Si(Li), Ge(Li), Silicon Drift Detector SDD) may be used in energy dispersive analysis. These detectors are based on the same principle: an incoming X-ray photon ionizes a large number of detector atoms with the amount of charge carriers produced being proportional to the energy of the incoming X-ray photon. The charge carriers are collected and counted to determine the energy of the incoming X-ray photon and the process repeats itself for the next incoming X-ray photon. After detection of many X-ray photons, a spectrum may be compiled by counting the number of X-ray photons as a function of their energy. The speed of these detectors is limited because the charge carriers generated by one incoming X-ray photon must be collected before the next incoming X-ray hits the detector.

Wavelength dispersive analysis typically uses a photomultiplier. The X-ray photons of a single wavelength are selected from the incoming X-ray a monochromator and are passed into the photomultiplier. The photomultiplier counts individual X-ray photons as they pass through. The counter is a chamber containing a gas that is ionizable by X-ray photons. A central electrode is charged at (typically) +1700 V with respect to the conducting chamber walls, and each X-ray photon triggers a pulse-like cascade of current across this field. The signal is amplified and transformed into an accumulating digital count. These counts are used to determine the intensity of the X-ray at the single wavelength selected.

SUMMARY

Disclosed herein is an X-ray source, comprising: a cathode in a recess of a first substrate; a counter electrode on a sidewall of the recess, configured to cause field emission of electrons from the cathode; and a metal anode configured to receive the electrons emitted from the cathode and to emit X-ray from impact by the electrons on the method anode.

According to an embodiment, the cathode comprises a plurality of carbon nanotubes.

According to an embodiment, the counter electrode is a continuous ring or dotted ring around the sidewall.

According to an embodiment, the X-ray source further comprises a shield electrode between the counter electrode and the metal anode, the shield electrode configured to repel the electrons away from the metal anode.

According to an embodiment, the shield electrode is a continuous ring or dotted ring around the sidewall.

According to an embodiment, the first substrate comprises silicon or silicon oxide.

According to an embodiment, the metal anode comprises one or more metals selected from a group consisting of tungsten, molybdenum, rhenium, copper and combinations thereof.

According to an embodiment, the X-ray source further comprises a second substrate bonded to the first substrate, wherein the second substrate covers the recess.

According to an embodiment, the metal anode is supported by the second substrate.

According to an embodiment, the metal anode is on a side of the second substrate facing the cathode.

According to an embodiment, the cathode comprises an array of carbon nanotubes.

Disclosed herein is a system comprising: a plurality of any of the above X-ray sources, a plurality of X-ray detectors, wherein the X-ray sources and the X-ray detectors are arranged alternately; an X-ray shield configured to prevent X-ray from the X-ray sources from directly reaching the X-ray detectors.

According to an embodiment, the X-ray shield is a layer of material between the X-ray detectors and the X-ray sources.

According to an embodiment, the layer of material comprises tungsten (W) or lead (Pb).

According to an embodiment, the layer of material has a thickness of 1.5-2 mm.

Disclosed herein is a system comprising any of the above X-ray sources and an X-ray detector, wherein the system is configured for performing X-ray radiography on human chest or abdomen.

Disclosed herein is a system comprising any of the above X-ray sources and an X-ray detector, wherein the system is configured for performing X-ray radiography on human mouth.

Disclosed herein is a cargo scanning or non-intrusive inspection (NII) system, comprising any of the above X-ray sources and an X-ray detector, wherein the cargo scanning or non-intrusive inspection (NII) system is configured for forming an image based on backscattered X-ray.

Disclosed herein is a cargo scanning or non-intrusive inspection (NII) system, comprising any of the above X-ray sources and an X-ray detector, wherein the cargo scanning or non-intrusive inspection (NII) system is configured for forming an image based on X-ray transmitted through an object inspected.

Disclosed herein is a full-body scanner system comprising any of the above X-ray sources and an X-ray detector.

Disclosed herein is an X-ray computed tomography (CT) system comprising any of the above X-ray sources and an X-ray detector.

Disclosed herein is a system suitable for phase-contrast X-ray imaging (PCI), the system comprising any of the above X-ray sources and an X-ray detector.

Disclosed herein is an electron microscope comprising any of the above X-ray sources.

Disclosed herein is a radiation dose meter comprising any of the above X-ray sources.

Disclosed herein is an element analyzer comprising any of the above X-ray sources.

Disclosed herein is a system suitable for detecting X-ray fluorescence (XRF), the system comprising any of the above X-ray sources and an X-ray detector.

BRIEF DESCRIPTION OF FIGURES

FIG. 3A schematically shows a top view of an X-ray source of the system of FIG. 2A, according to an embodiment.

FIG. 3B schematically shows a top view of an X-ray detector of the system of FIG. 2A, according to an embodiment.

DETAILED DESCRIPTION

Figure 1A:
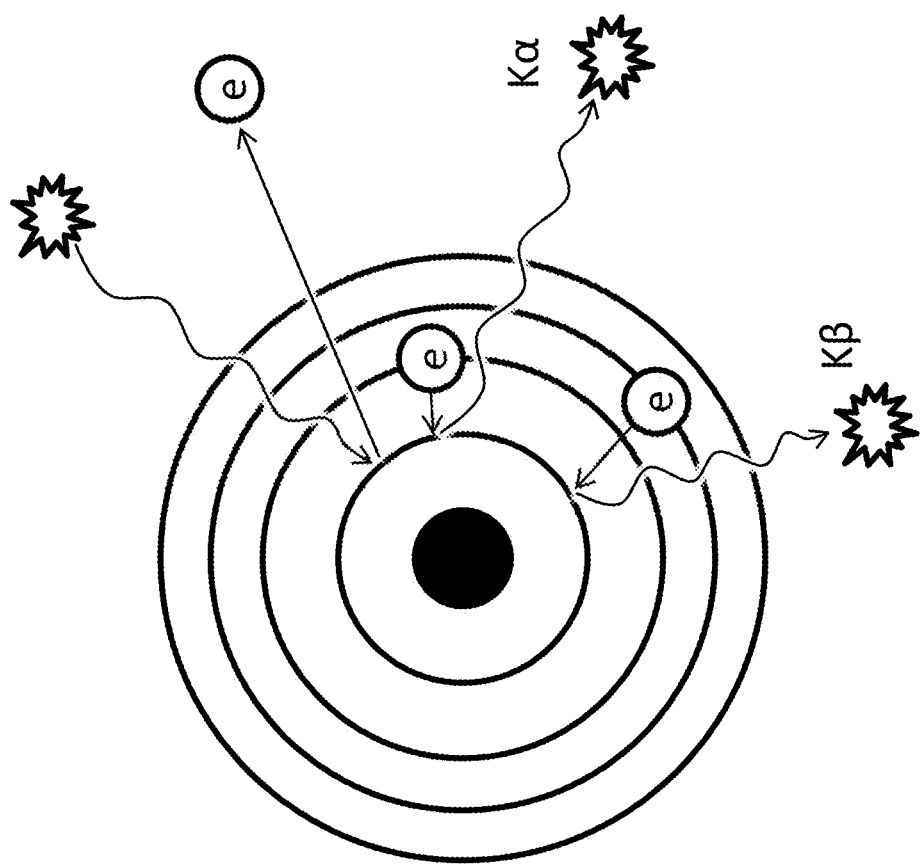
FIG. 1A and FIG. 1B schematically show mechanisms of XRF.
Figure 1B:
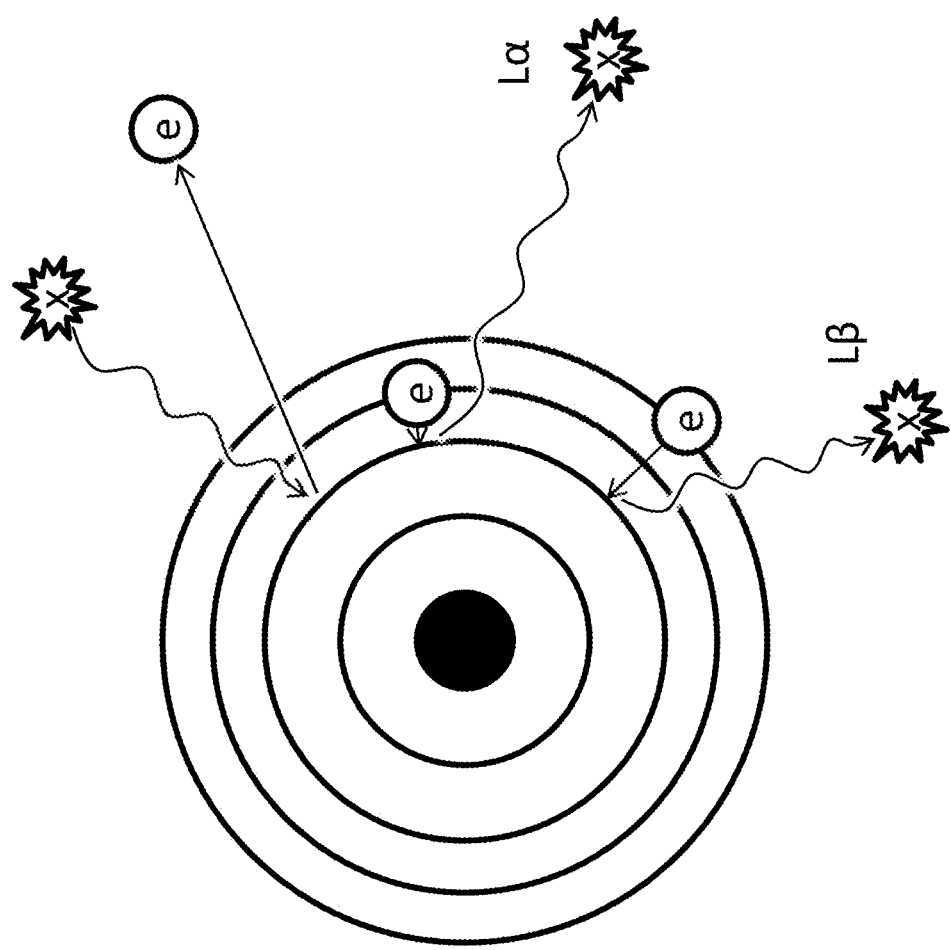
Figure 2A:
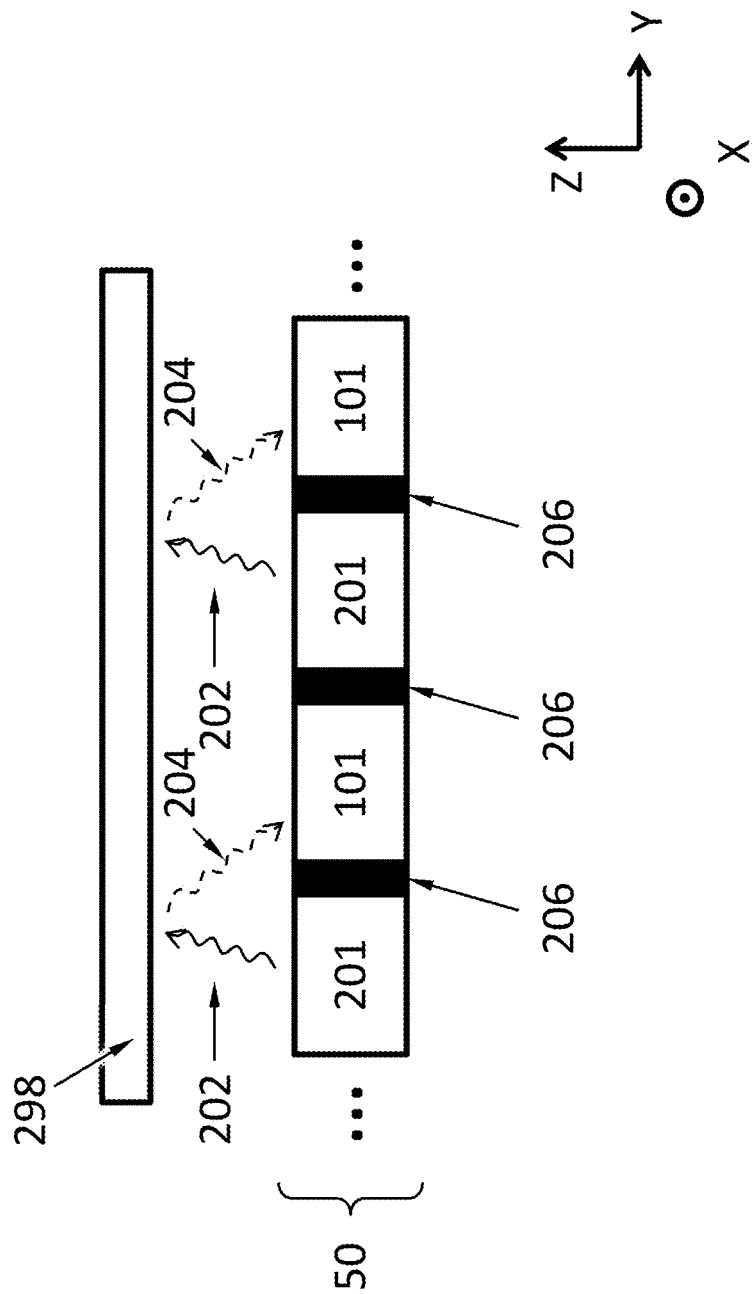
FIG. 2A schematically shows a system suitable for XRF, according to an embodiment.

FIG. 2A schematically shows a system 50 suitable for XRF, according to an embodiment. As shown, the system 50 includes a plurality of X-ray sources 201 and X-ray detectors 101. In an embodiment, the plurality of X-ray sources 201 and X-ray detectors 101 may be in a form of chips mounted on a printed circuit board (PCB). In an embodiment, the plurality of X-ray sources 201 and X-ray detectors 101 may be arranged in an alternating manner. The system 50 may include an X-ray shield configured to prevent X-ray from the X-ray sources 201 from directly reaching the X-ray detectors 101. The X-ray shield may include a layer of material 206 separating each of the X-ray sources 201 from and the X-ray detectors 101. In an embodiment, the layer of material 206 may include, but is not limited to, tungsten (W) or lead (Pb). In an embodiment, the layer of material 206 has a thickness of 1.5-2 millimeters (mm).

The X-ray photons 202 from the X-ray sources 201 may incident on a material sample 298. When the X-ray photons 202 have greater energies than the ionization potential of electrons on an inner orbital of an atom of the material sample 298, the electrons on the inner orbital of the atom may be ejected, leaving a vacancy on the inner orbital. When an electron on an outer orbital of the atom relaxes to fill the vacancy on the inner orbital, a fluorescent X-ray ray photon 204 (also referred to as a secondary X-ray photon) is emitted. The fluorescent X-ray photon 204 has energy equal to the energy difference between the outer orbital and inner orbital electrons.

The X-ray detector 101 may be configured to receive the fluorescent X-ray photons 204 and identify the element of the material sample 298 by analyzing the received fluorescent X-ray photons 204.

Figure 2B:
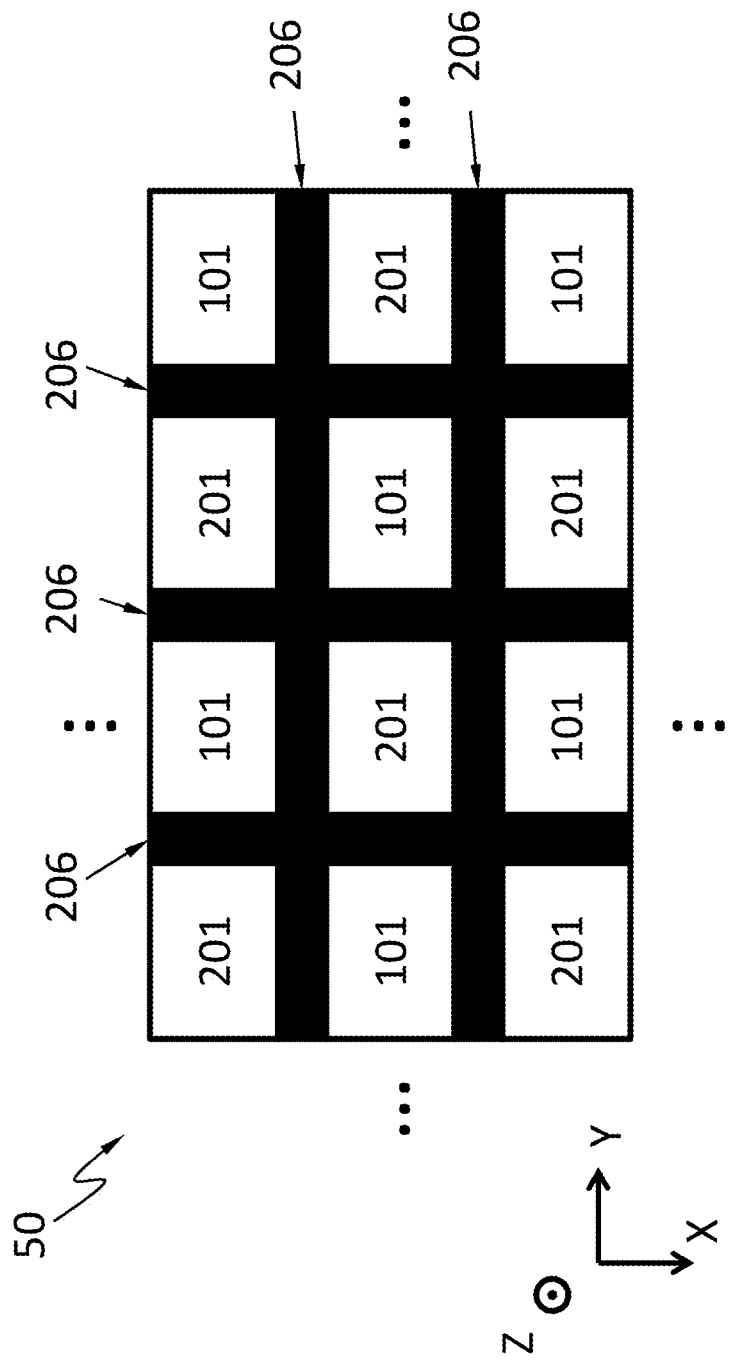
FIG. 2B schematically shows a top view of the system of FIG. 2A, according to an embodiment.

FIG. 2B schematically shows a top view of the system 50, according to an embodiment. As shown, the system 50 includes a plurality of X-ray sources 201 and a plurality of X-ray detectors 101, arranged in an alternating manner like a checker board. Also as shown, the X-ray sources 201 and X-ray detectors 101 may be separated by the layer of material 206.

Figure 2C:
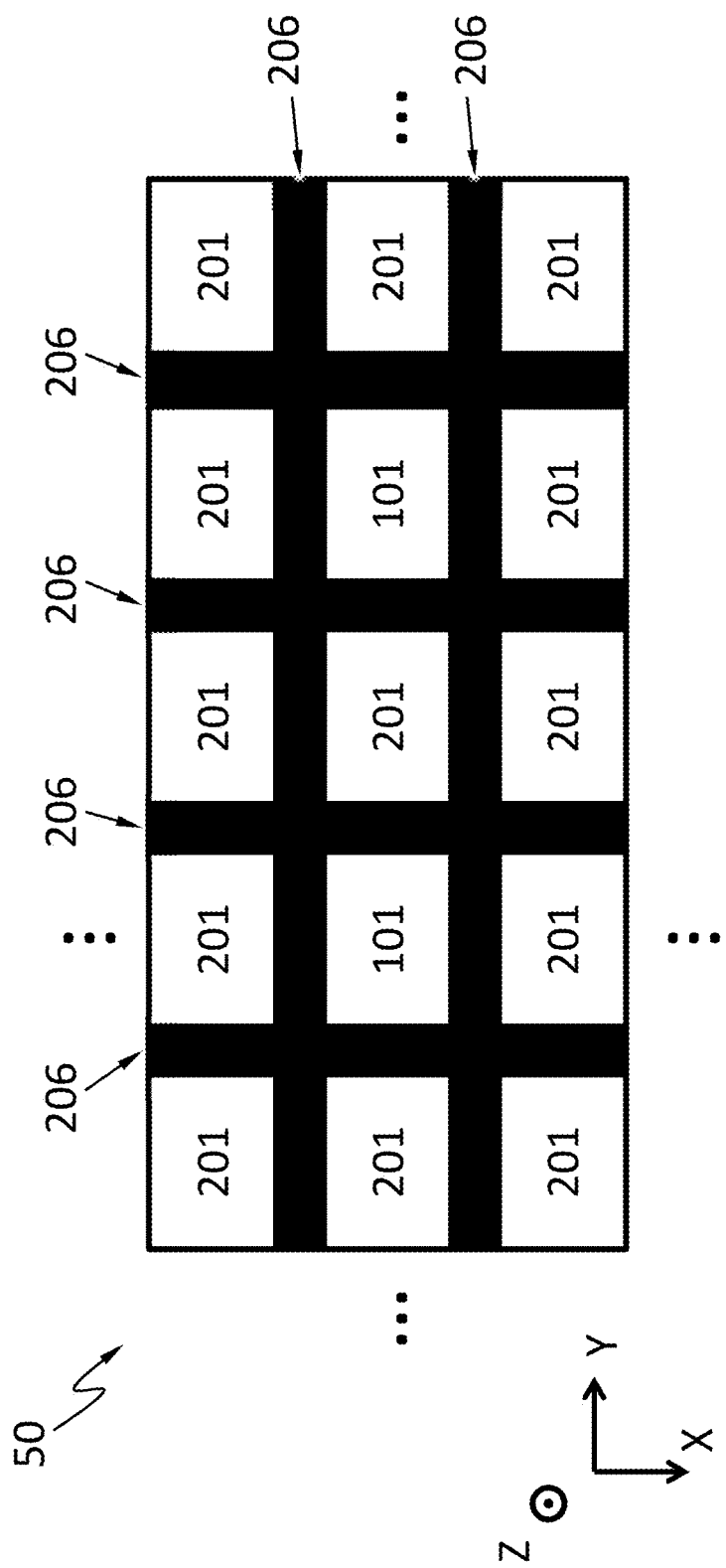
FIG. 2C schematically shows a top view of the system of FIG. 2A, according to an embodiment.

FIG. 2C schematically shows a top view of the system 50, according to an embodiment. As shown, the system 50 includes a plurality of X-ray sources 201 and a plurality of X-ray detectors 101, arranged in such a way that each of the X-ray detectors 101 is surrounded by X-ray sources 201. Also as shown, the X-ray sources 201 and X-ray detectors 101 may be separated by the layer of material 206.

FIG. 3A schematically shows a top view of the X-ray source 201 of the system 50, according to an embodiment. As shown, the X-ray source 201 includes a plurality of X-ray generators 299 arranged in an array. In this example, the X-ray source 201 includes a plurality of rows of X-ray generators 299. In some examples, the X-ray source 201 may include only one row or one column of X-ray generators 299.

FIG. 3B schematically shows a top view of the X-ray detector 101 of the system 50, according to an embodiment. As shown, the X-ray detector 101 includes a plurality of pixels 199 arranged in an array. In this example, the X-ray detector 101 includes a plurality of rows of pixels 199. In some examples, the X-ray detector 101 may include only one row or one column of pixels 199.

Figure 4:
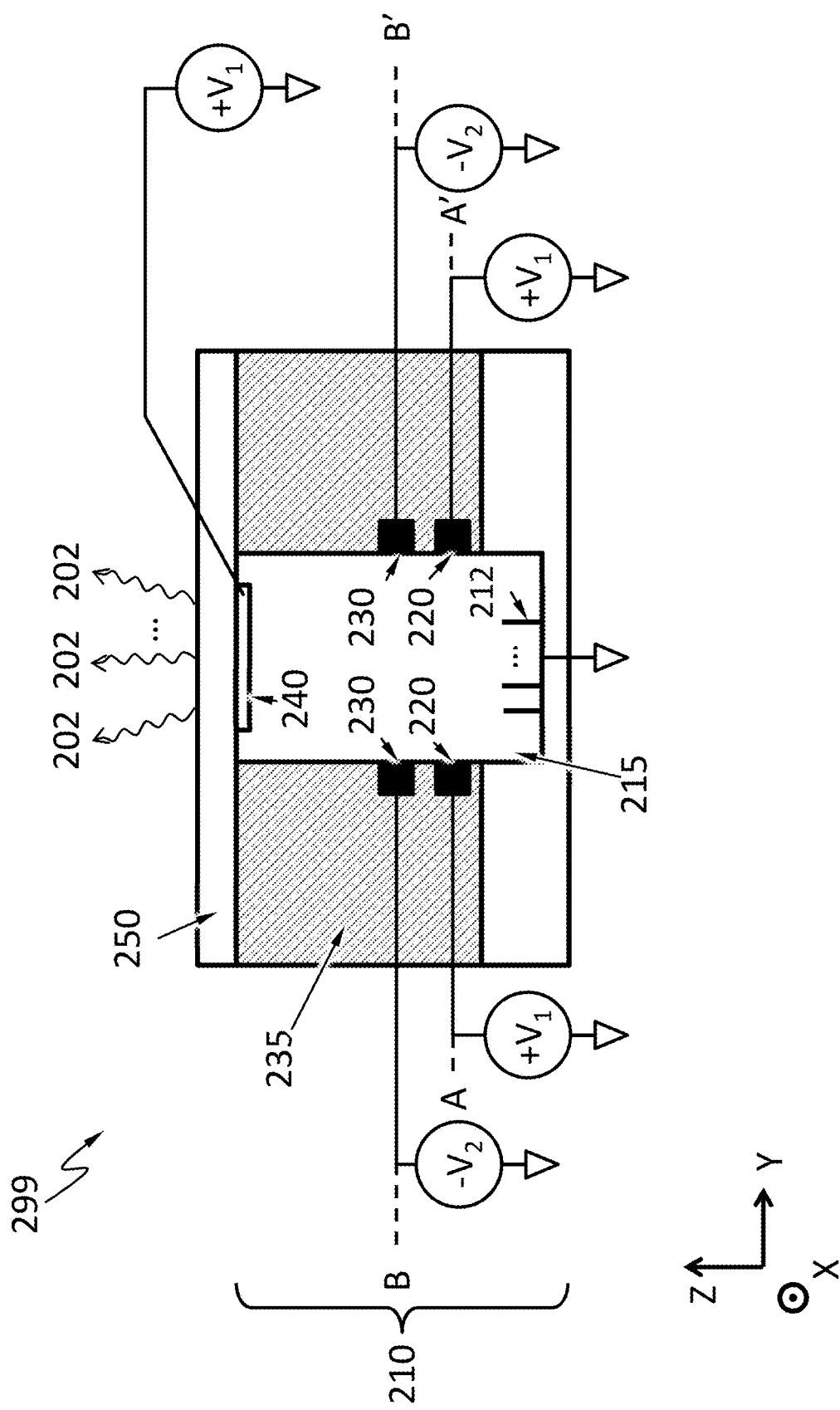
FIG. 4 schematically shows a cross-sectional view of an X-ray generator of the X-ray source, according to an embodiment.

FIG. 4 schematically shows a cross-sectional view of the X-ray generator 299, according to an embodiment. In this example, the X-ray generator 299 includes a first substrate 210, a cathode 212 (e.g., a plurality of carbon nanotubes), a counter electrode 220, optionally a shield electrode 230, a metal anode 240, and optionally a second substrate 250.

In an embodiment, the first substrate 210 may include, but is not limited to, silicon or silicon oxide. As shown, the first substrate 210 has a recess 215. The cathode 212 is formed in the recess 215 of the first substrate 210. The cathode 212 in the recess 215 may include one or more than one carbon nanotubes. The cathode 212 may be configured to emit electrons under an electric field. Electrons may be bound in the cathode 212 (e.g., carbon nanotubes) by a surface potential energy barrier. When a sufficiently strong electrical field is applied (e.g., along the length direction of the carbon nanotubes) to the cathode 212, the electrons in the cathode 212 may acquire sufficient energy and overcome the surface potential energy barrier of the cathode 212 and enter the free space in the recess 215. This mechanism of producing electrons into free space may be referred to as field emission. In an embodiment, the cathode 212 is electrically grounded.

In an embodiment, the counter electrode 220 is on a sidewall of the recess 215. The counter electrode 220 may be biased to a positive voltage of $+V_1$ relative to the cathode 212 thereby provide the electrical field to cause field emission of electrons from the cathode 212. As described above, the electric field established by the positive voltage $+V_1$ may provide the bounded electrons in the cathode 212 with energies greater than the surface potential energy barrier. Also as shown in FIG. 4, the counter electrode 220 may be electrically insulated by an insulator 235 of the first substrate 210.

Figure 5A:
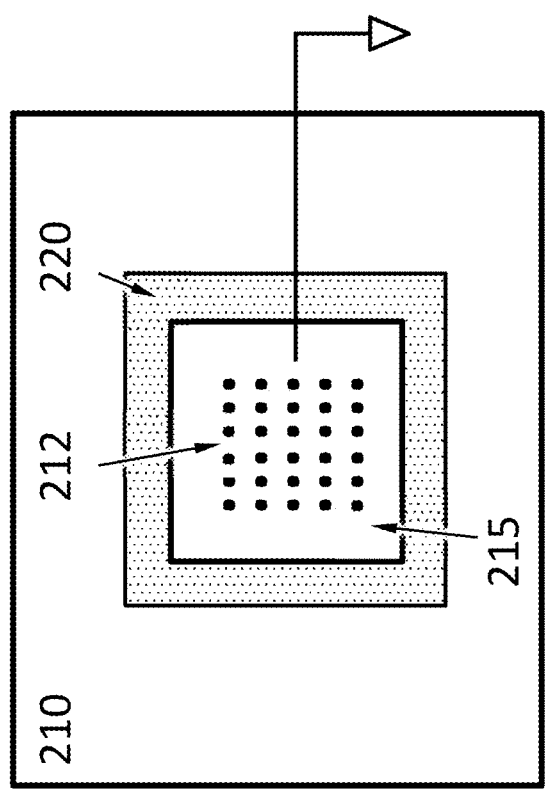
FIG. 5A schematically shows a top view toward a cross-section of the X-ray generator along an A-A' cutline in FIG. 4, according to an embodiment.

FIG. 5A schematically shows a top view toward a cross-section of the X-ray generator 299 along an A-A' cutline in FIG. 4, according to an embodiment. In this example, only the cross sections of the first substrate 210, the cathode 212, the counter electrode 220 and the recess 215 in FIG. 4 are shown. As shown, the cathode 212 may be carbon nanotubes arranged in an array and connected electrically to the ground. In this specific example, the carbon nanotubes are arranged in a rectangular array. However, in some other examples, the nanotubes may be arranged in any other suitable shape of array, including, but not limited to, a circular array, a hexagonal array, and a honeycomb array. The carbon nanotubes may also have no particular arrangement. Also as shown, the counter electrode 220 may be a continuous ring or dotted ring around the sidewall of the recess 215 of the first substrate 210. Electric connections to the counter electrode 220 are not shown for brevity. In this example, the counter electrode 220 is arranged along the entire perimeter of the sidewall. In some other examples, the counter electrode 220 may be arranged along part of the perimeter of the sidewall. In the example shown in FIG. 5A, the recess 215 has a rectangular cross section and the counter electrode 220 may also be rectangular.

Figure 5B:
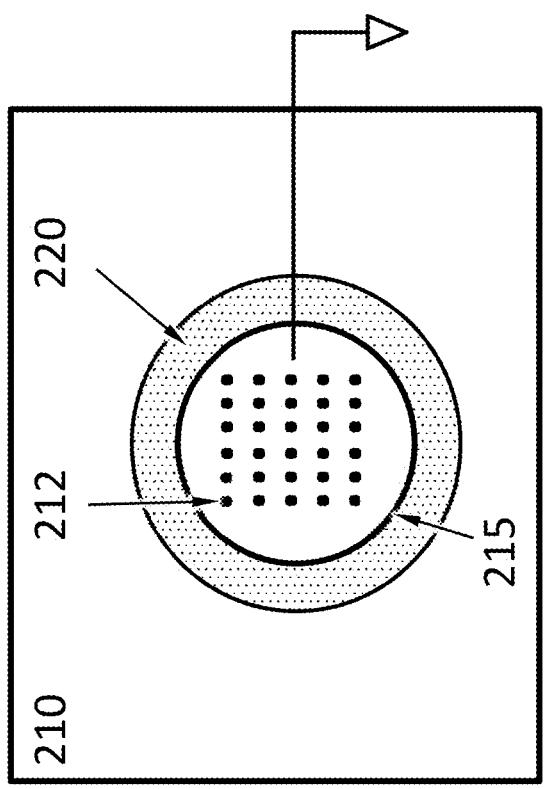
FIG. 5B schematically shows a top view toward a cross-section of the X-ray generator along an A-A' cutline in FIG. 4, according to another embodiment.

FIG. 5B schematically shows the top view toward the cross-section of the X-ray generator 299 along an A-A' cutline in FIG. 4, according to another embodiment. Different from FIG. 5A, the cross section of the recess 215 is circular, and the counter electrode 220 may also be circular.

Returning to FIG. 4, the shield electrode 230 may be on the sidewall of the recess 215 and between the counter electrode 220 and the metal anode 240. The shield electrode 230 may be suitably biased to repel the electrons emitted from the anode 212 away from the metal anode 240 and thus function as a switch of the X-ray generator 299 (i.e., to enable or disable the generation of the X-ray photons 202 by the X-ray generator 299). As shown, the shield electrode 230 may electrically insulated from the counter electrode 220, and the counter electrode 220 by the insulator 235. Further as shown, the shield electrode 230 may not necessarily be exposed in the recess 215. In an embodiment, the shield electrode 230 may have a similar shape as the counter electrode 220.

When the shield electrode 230 is provided with a sufficiently negative voltage of $-V_2$ relative to the cathode 212, the shield electrode 230 may repel the electrons emitted from the cathode 212 away from the metal anode 240. Without electrons impacting the metal anode 240, the generation of X-ray photons 202 is disabled. When the shield electrode 230 is not sufficiently negatively biased, electrons from the cathode 212 may impact the metal anode 240 and the generation of X-ray photons 202 is enabled.

Figure 6A:
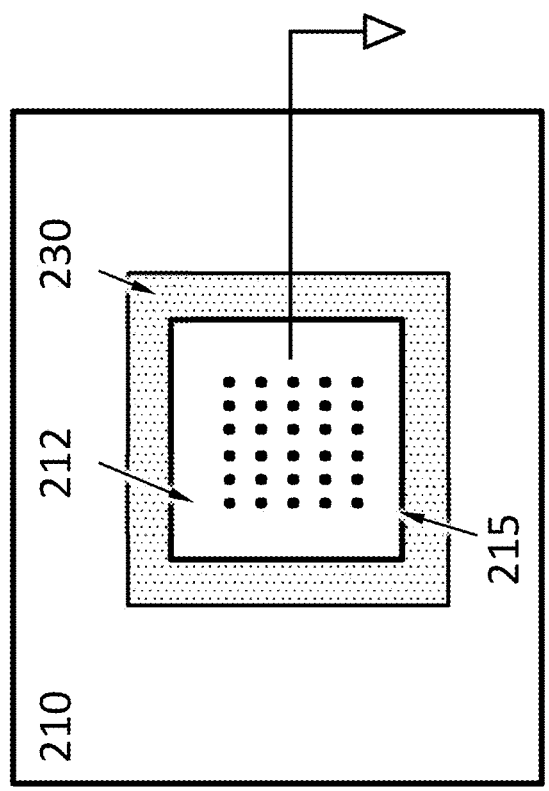
FIG. 6A schematically shows a top view toward a cross-section of the X-ray generator along a B-B' cutline in FIG. 4, according to an embodiment.

FIG. 6A schematically shows a top view toward a cross-section of the X-ray generator 299 along a B-B' cutline in FIG. 4, according to an embodiment. In this example, only the cross sections of the first substrate 210, the cathode 212, and the shield electrode 230 in FIG. 4 are shown. As shown, the cathode 212 may be carbon nanotubes arranged in an array and connected electrically to the ground. In this specific example, the carbon nanotubes are arranged in a rectangular array. However, in some other examples, the nanotubes may be arranged in any other suitable shape of array, including, but not limited to, a circular array, a hexagonal array, and a honeycomb array. The carbon nanotubes may also have no particular arrangement. Also as shown, the shield electrode 230 may be a continuous ring or dotted ring around the sidewall of the recess 215 of the first substrate 210. Electric connections to the shield electrode 230 are not shown for brevity. In this example, the shield electrode 230 is arranged along the entire perimeter of the sidewall. In some other examples, the shield electrode 230 may be arranged along part of the perimeter of the sidewall. In the example shown in FIG. 6A, the recess 215 has a rectangular cross section and the shield electrode 230 may also be rectangular.

Figure 6B:
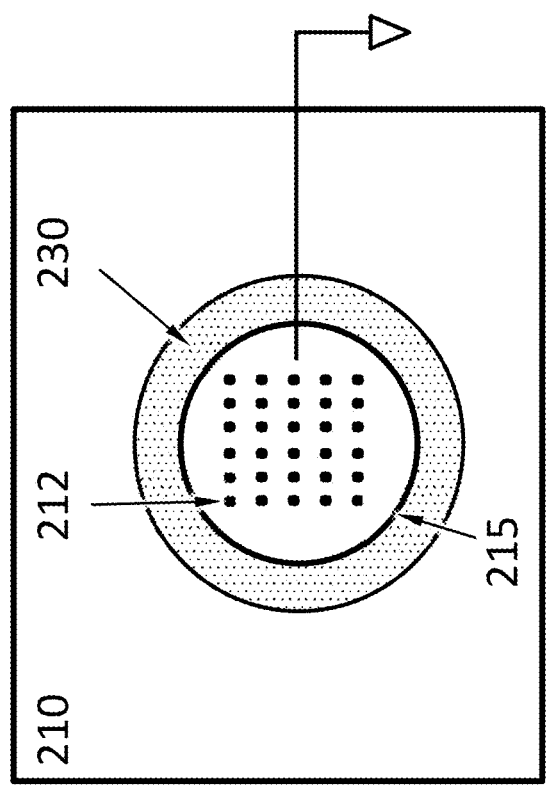
FIG. 6B schematically shows a top view toward a cross-section of the X-ray generator along a B-B' cutline in FIG. 4, according to another embodiment.

FIG. 6B schematically shows the top view toward the cross-section of the X-ray generator 299 along a B-B' cutline in FIG. 4, according to another embodiment. Different from FIG. 6A, the cross section of the recess 215 is circular, and the shield electrode 230 may also be circular.

Returning to FIG. 4, in an embodiment, the second substrate 250 may be a glass substrate or a substrate that has low attenuation of X-ray of interest. In an embodiment, the second substrate 250 may include, but is not limited to, silicon or silicon oxide. The second substrate 250 may allow X-ray photons 202 to pass through. As shown, the metal anode 240 is beneath the second substrate 250 (i.e., on the side facing the cathode 212), which are collectively situated on the insulator 235. In another embodiment, the metal anode 240 may be dispose over the recess 215 without the second substrate 250.

The metal anode 240 may be biased to a positive voltage of $+V_3$ relative to the cathode 212. The electrons from the anode 212, if not repelled by the shield electrode 230, are accelerated by an electric field established by this voltage toward the metal anode 240. The metal anode 240 may include, but is not limited to, tungsten, molybdenum, rhenium, copper, or their combinations. When the electrons gain enough kinetic energy (e.g., greater than 10 KeV, 50 KeV, 80 KeV, 100 KeV, 130 KeV, etc.) before hitting the metal anode 240, the X-ray photons 202 may be generated after the high speed free electrons impact the metal anode 240.

Figure 7:
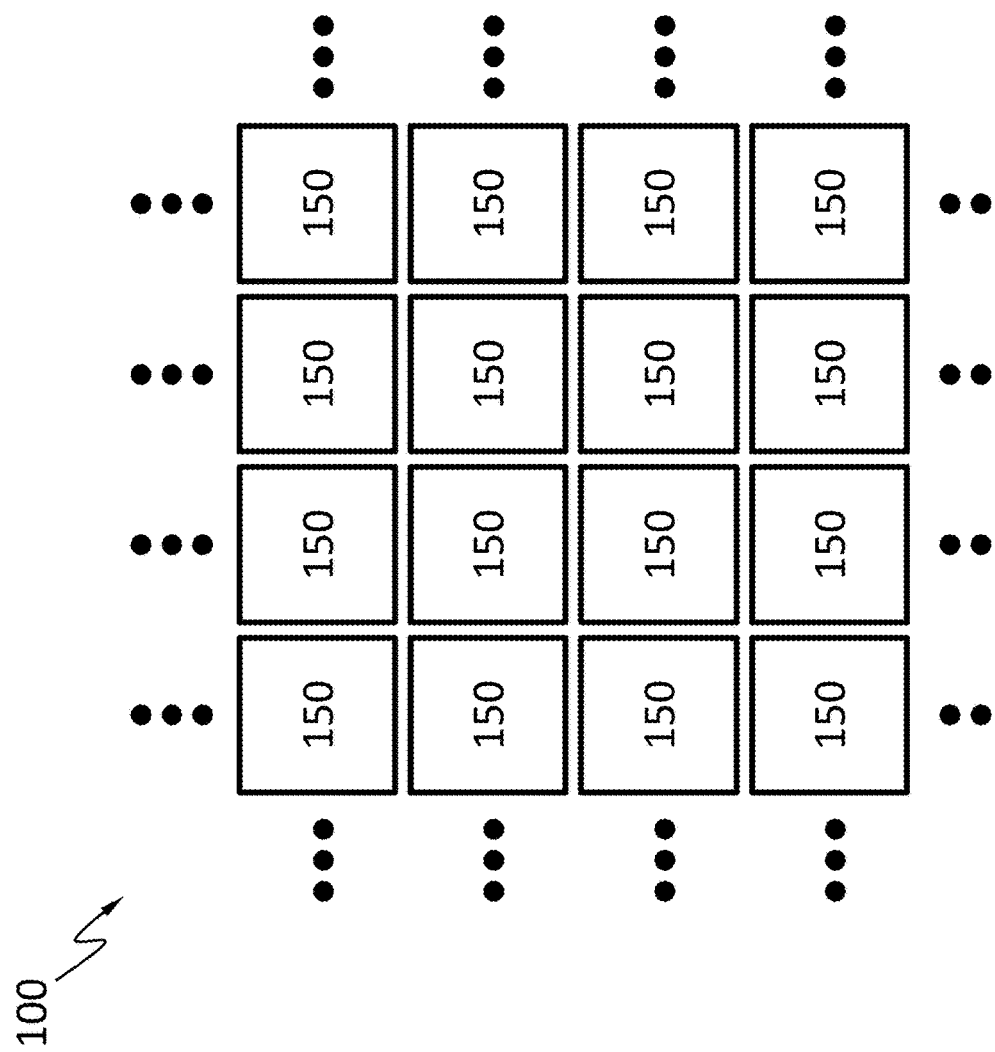
FIG. 7 schematically shows an X-ray detector that may be used with the X-ray source, according to an embodiment.

FIG. 7 schematically shows an X-ray detector 100 suitable for using with the X-ray source 201, according to an embodiment. The detector has an array of pixels 150. The array may be a rectangular array, a honeycomb array, a hexagonal array or any other suitable array. Each pixel 150 is configured to detect an X-ray photon incident thereon and measure the energy of the X-ray photon. For example, each pixel 150 is configured to count numbers of X-ray photons incident thereon whose energy falls in a plurality of bins, within a period of time. All the pixels 150 may be configured to count the numbers of X-ray photons incident thereon within a plurality of bins of energy within the same period of time. Each pixel 150 may have its own analog-to-digital converter (ADC) configured to digitize an analog signal representing the energy of an incident X-ray photon into a digital signal. For XRF applications, an ADC with a 10-bit resolution or higher is useful. Each pixel 150 may be configured to measure its dark current, such as before or concurrently with each X-ray photon incident thereon. Each pixel 150 may be configured to deduct the contribution of the dark current from the energy of the X-ray photon incident thereon. The pixels 150 may be configured to operate in parallel. For example, when one pixel 150 measures an incident X-ray photon, another pixel 150 may be waiting for an X-ray photon to arrive. The pixels 150 may not have to be individually addressable.

The detector 100 may have at least 100, 2500, 10000, or more pixels 150. The detector 100 may be configured to add the numbers of X-ray photons for the bins of the same energy range counted by all the pixels 150. For example, the detector 100 may add the numbers the pixels 150 stored in a bin for energy from 70 KeV to 71 KeV, add the numbers the pixels 150 stored in a bin for energy from 71 KeV to 72 KeV, and so on. The detector 100 may compile the added numbers for the bins as a spectrum of the X-ray photons incident on the detector 100.

Figure 8:
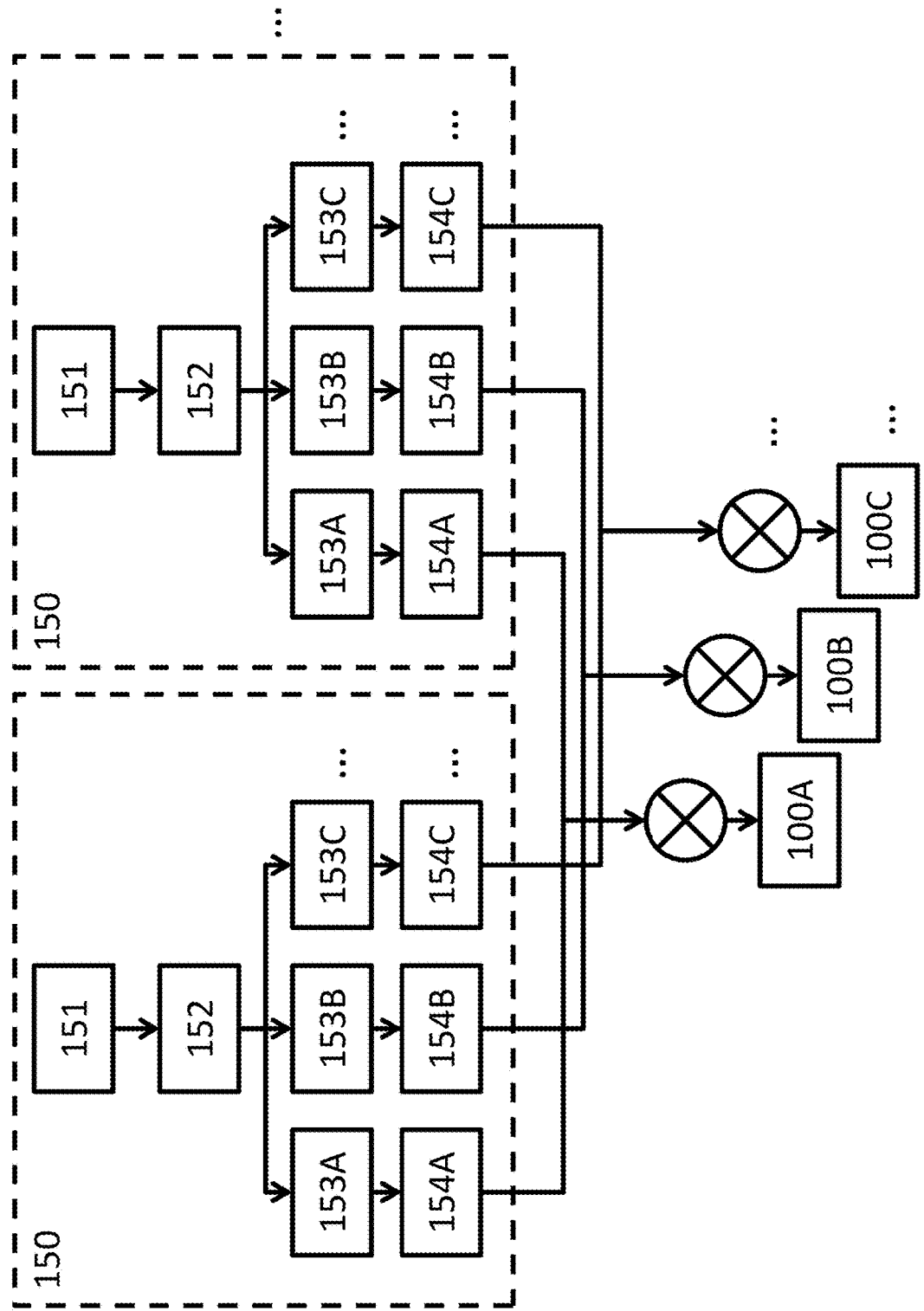
FIG. 8 schematically shows a block diagram for the detector, according to an embodiment.

FIG. 8 schematically shows a block diagram for the detector 100, according to an embodiment. Each pixel 150 may measure the energy of an X-ray photon incident thereon in step 151. The energy of the X-ray photon is digitized (e.g., by an ADC) in step 152 into one of a plurality of bins 153A, 153B, 153C . . . . The bins 153A, 153B, 153C . . . each have a corresponding counter 154A, 154B and 154C, respectively. When the energy is allocated into a bin, the number stored in the corresponding counter increases by one. The detector 100 may added the numbers stored in all the counters corresponding to bins for the same energy range in the pixels 150. For example, the numbers stored in all the counters (e.g., 154A, 154B, 154C) in all pixels 150 may be added and stored in a global counter (e.g., 100A, 100B, 100C) for the same energy range. The numbers stored in all the global counters may be compiled into an energy spectrum of the X-ray incident on the detector 100.

Figure 9A:
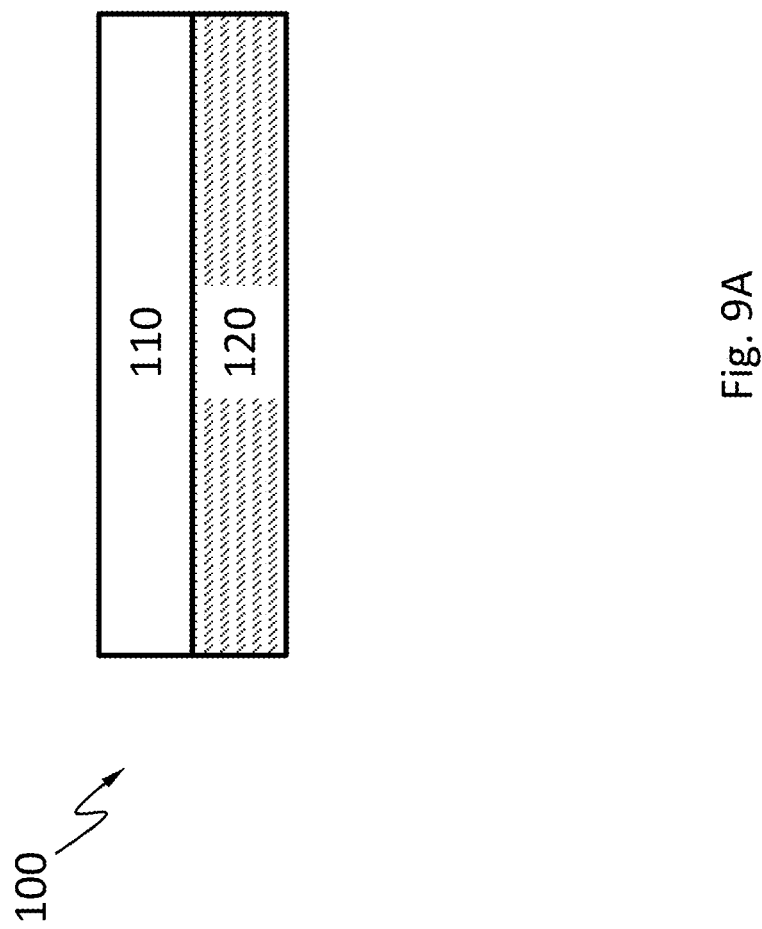
FIG. 9A schematically shows a cross-sectional view of the detector, according to an embodiment.

FIG. 9A schematically shows a cross-sectional view of the detector 100, according to an embodiment. The detector 100 may include an X-ray absorption layer 110 and an electronics layer 120 (e.g., an ASIC) for processing or analyzing electrical signals incident X-ray generates in the X-ray absorption layer 110. In an embodiment, the detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 9B:
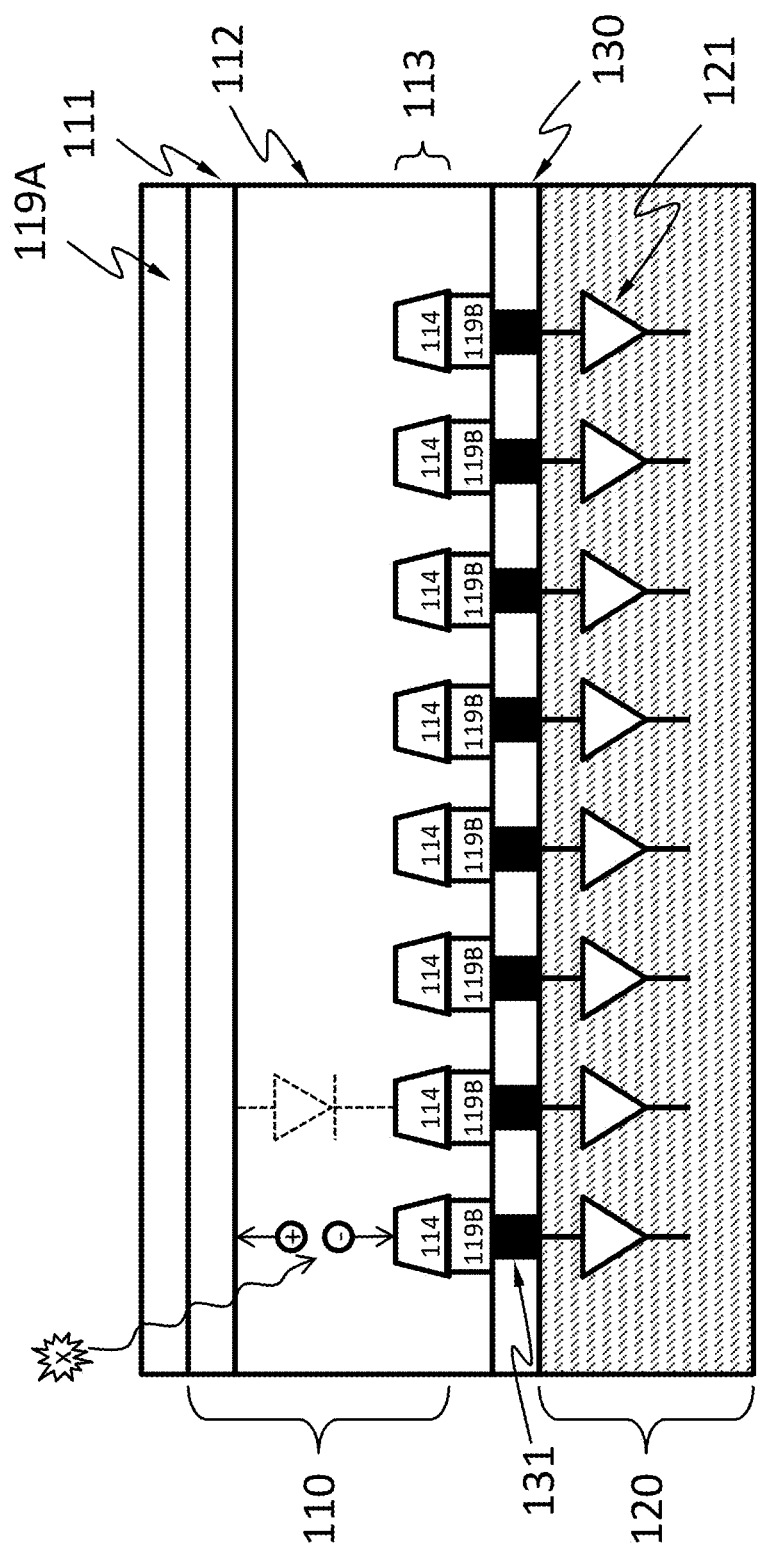
FIG. 9B schematically shows a detailed cross-sectional view of the detector, according to an embodiment.

As shown in a detailed cross-sectional view of the detector 100 in FIG. 9B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 8B, each of the discrete regions 114 of the second doped region 113 forms a diode with the first doped region 111 and the optional intrinsic region 112. Namely, in the example in FIG. 8B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single X-ray photon are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by an X-ray photon incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by an X-ray photon incident therein flow to the discrete region 114. Namely, less than 2%, less than 1%, less than 0.1%, or less than 0.01% of these charge carriers flow beyond the pixel.

Figure 9C:
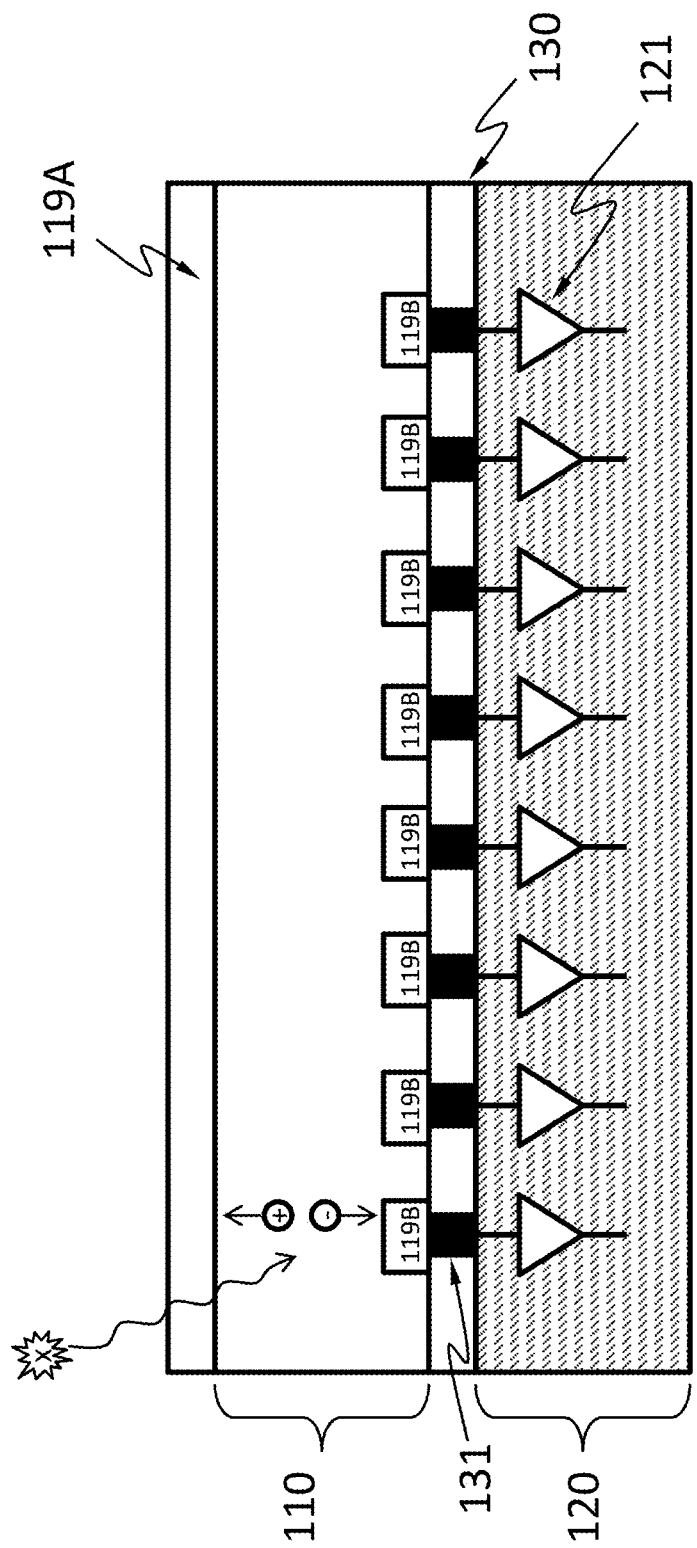
FIG. 9C schematically shows an alternative detailed cross-sectional view of the detector, according to an embodiment.

As shown in an alternative detailed cross-sectional view of the detector 100 in FIG. 9C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single X-ray photon are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by an X-ray photon incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by an X-ray photon incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 10A:
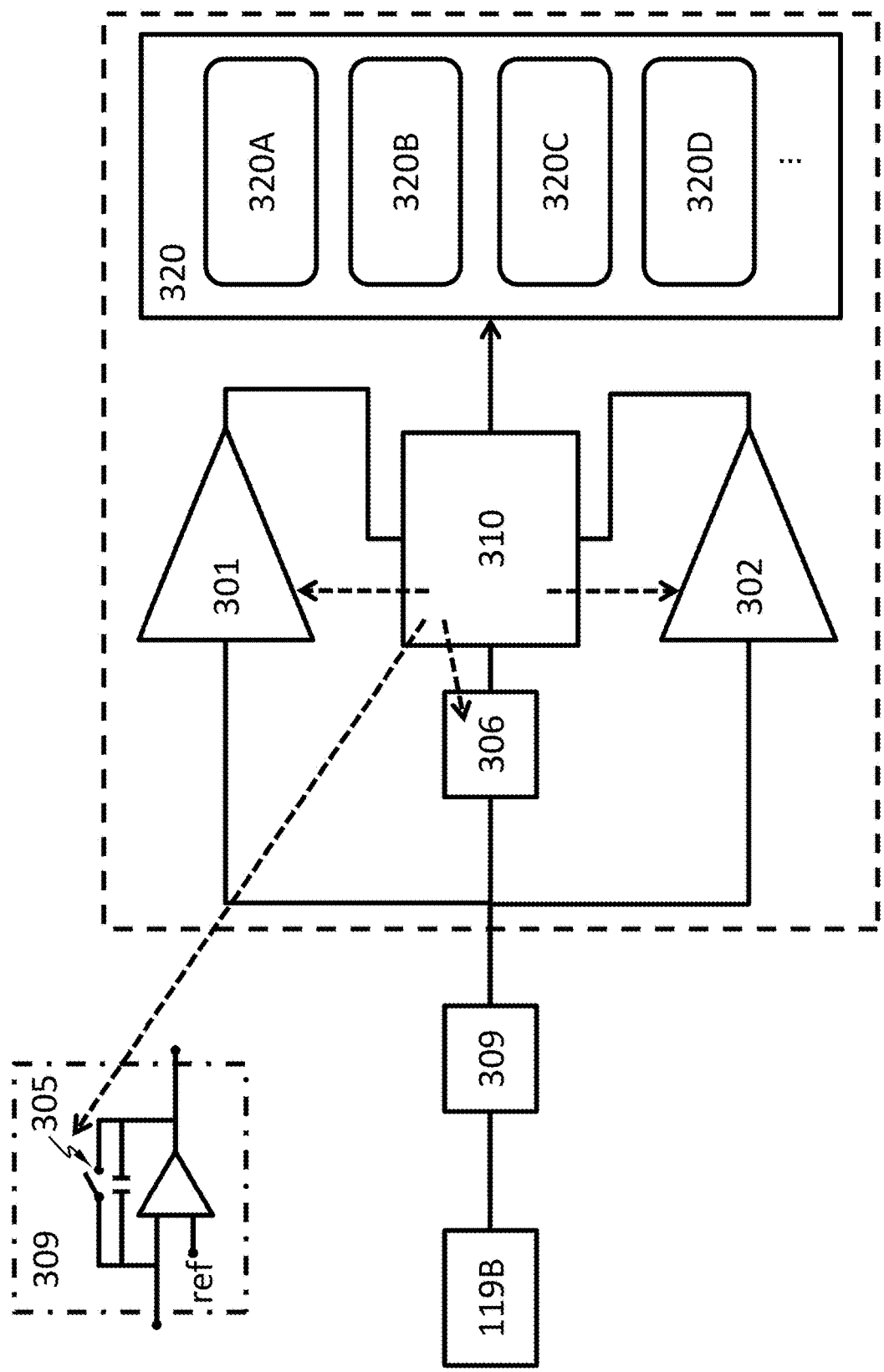
FIG. 10A and FIG. 10B each schematically show a component diagram of the electronic system of the detector, according to an embodiment.
Figure 10B:
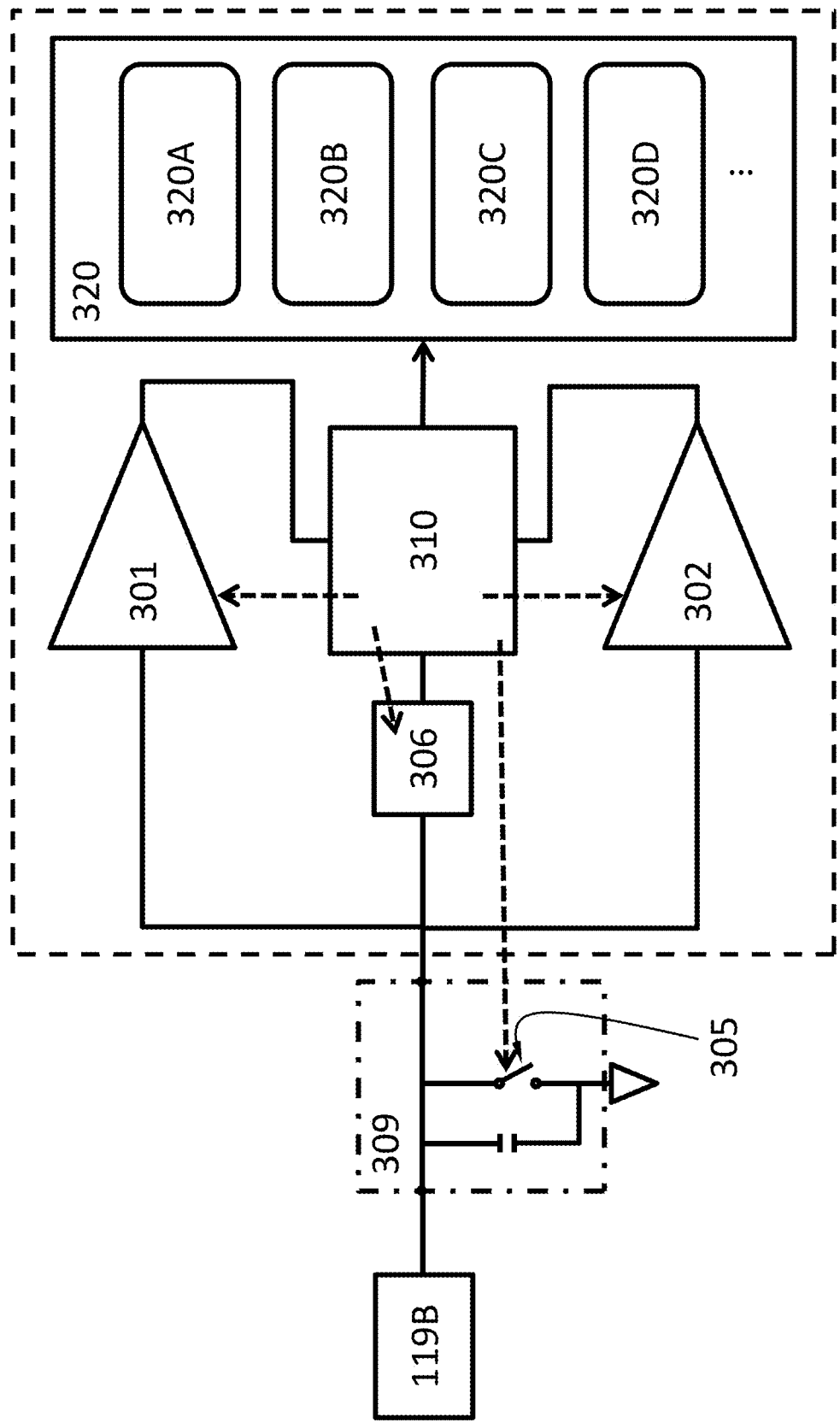

FIG. 10A and FIG. 10B each show a component diagram of the electronic system 121, according to an embodiment. The electronic system 121 may include a first voltage comparator 301, a second voltage comparator 302, a plurality of counters 320 (including counters 320A, 320B, 320C, 320D . . . ), a switch 305, an ADC 306 and a controller 310.

The first voltage comparator 301 is configured to compare the voltage of a discrete portion of the electric contact 119B to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 1-5%, 5-10%, 10%-20%, 20-30%, 30-40% or 40-50% of the maximum voltage one incident X-ray photon may generate on the electric contact 119B. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counters 320 may be a software component (e.g., numbers stored in a computer memory) or a hardware component (e.g., 4017 IC and 7490 IC). Each counter 320 is associated with a bin for an energy range. For example, counter 320A may be associated with a bin for 70-71 KeV, counter 320B may be associated with a bin for 71-72 KeV, counter 320C may be associated with a bin for 72-73 KeV, counter 320D may be associated with a bin for 73-74 KeV. When the energy of an incident X-ray photons is determined by the ADC 306 to be in the bin a counter 320 is associated with, the number registered in the counter 320 is increased by one.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire after the voltage becomes stable, i.e., the rate of change of the voltage is substantially zero. The phase "the rate of change is substantially zero" means that temporal change is less than 0.1%/ns. The phase "the rate of change is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by one of the counters 320 to increase by one, if, during the time delay, the second voltage comparator 302 determines that the absolute value of the voltage equals or exceeds the absolute value of the second threshold, and the energy of the X-ray photon falls in the bin associated with the counter 320.

The controller 310 may be configured to cause the ADC 306 to digitize the voltage upon expiration of the time delay and determine based on the voltage which bin the energy of the X-ray photon falls in.

The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The ADC 306 may feed the voltage it measures to the controller 310 as an analog or digital signal. The ADC may be a successive-approximation-register (SAR) ADC (also called successive approximation ADC). An SAR ADC digitizes an analog signal via a binary search through all possible quantization levels before finally converging upon a digital output for the analog signal. An SAR ADC may have four main subcircuits: a sample and hold circuit to acquire the input voltage ($V_{in}$), an internal digital-analog converter (DAC) configured to supply an analog voltage comparator with an analog voltage equal to the digital code output of the successive approximation register (SAR), the analog voltage comparator that compares $V_{in}$ to the output of the internal DAC and outputs the result of the comparison to the SAR, the SAR configured to supply an approximate digital code of $V_{in}$ to the internal DAC. The SAR may be initialized so that the most significant bit (MSB) is equal to a digital 1. This code is fed into the internal DAC, which then supplies the analog equivalent of this digital code ($V_{ref}/2$) into the comparator for comparison with $V_{in}$. If this analog voltage exceeds $V_{in}$ the comparator causes the SAR to reset this bit; otherwise, the bit is left a 1. Then the next bit of the SAR is set to 1 and the same test is done, continuing this binary search until every bit in the SAR has been tested. The resulting code is the digital approximation of $V_{in}$ and is finally output by the SAR at the end of the digitization.

Figure 11:
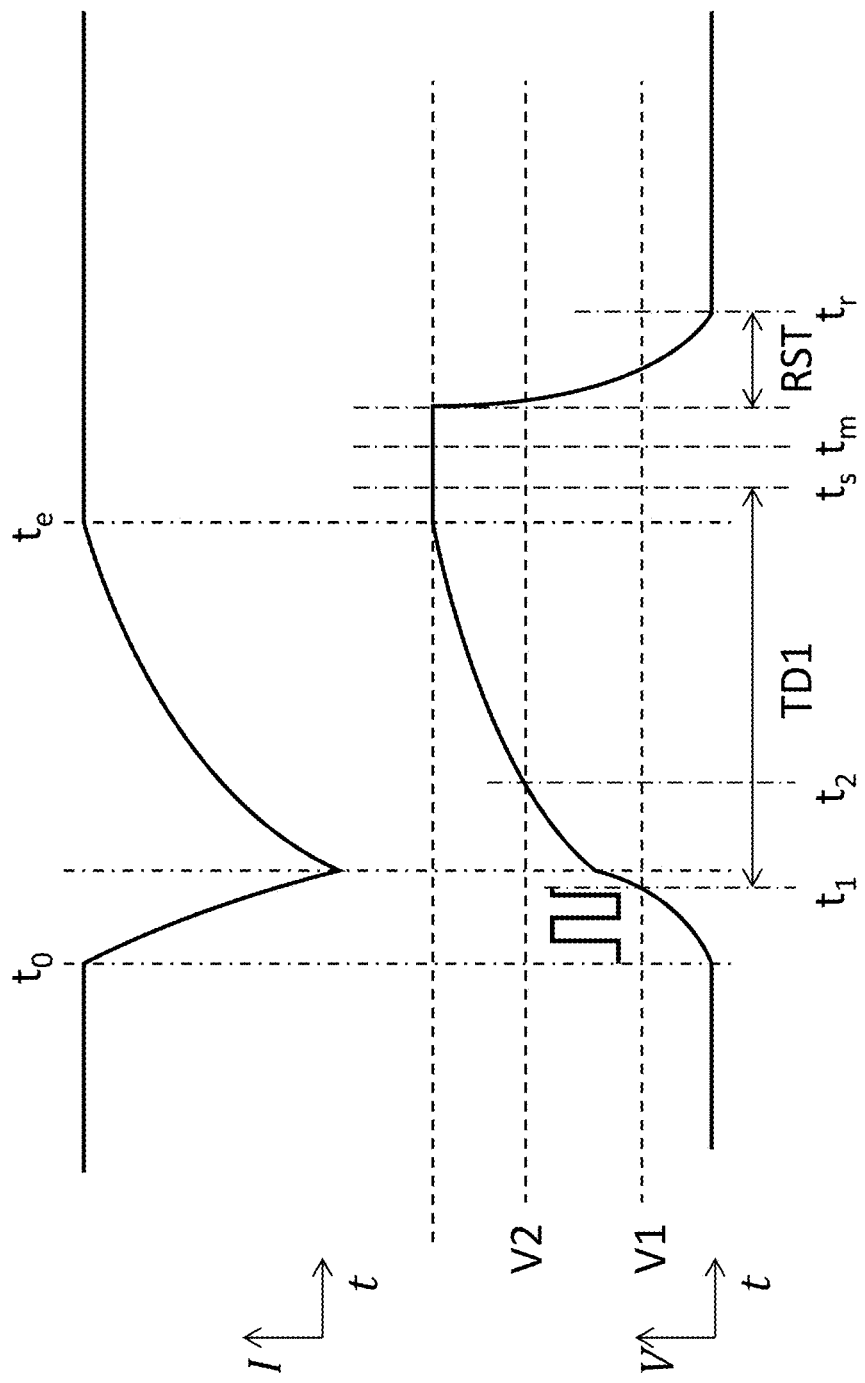
FIG. 11 schematically shows a temporal change of the electric current flowing through an electric contact (upper curve) caused by charge carriers generated by an X-ray photon incident on a pixel associated with the electric contact, and a corresponding temporal change of the voltage of the electric contact (lower curve).

The system 121 may include a capacitor module 309 electrically connected to the electric contact 119B, wherein the capacitor module is configured to collect charge carriers from the electric contact 119B. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 11, between $t_s$ to $t_0$). After the integration period has expired, the capacitor voltage is sampled by the ADC 306 and then reset by a reset switch. The capacitor module 309 can include a capacitor directly connected to the electric contact 119B.

FIG. 11 schematically shows a temporal change of the electric current flowing through the electric contact 119B (upper curve) caused by charge carriers generated by an X-ray photon incident on the pixel 150 associated with the electric contact 119B, and a corresponding temporal change of the voltage of the electric contact 119B (lower curve). The voltage may be an integral of the electric current with respect to time. At time $t_0$, the X-ray photon hits the diode or the resistor, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 waits for stabilization of the voltage to stabilize. The voltage stabilizes at time $t_e$, when all charge carriers generated by the X-ray photon drift out of the X-ray absorption layer 110. At time $t_s$, the time delay TD1 expires. At or after time $t_e$, the controller 310 causes the ADC 306 to digitize the voltage and determines which bin the energy of the X-ray photons falls in. The controller 310 then causes the number registered by the counter 320 corresponding to the bin to increase by one. In the example of FIG. 11, time $t_s$ is after time $t_e$; namely TD1 expires after all charge carriers generated by the X-ray photon drift out of the X-ray absorption layer 110. If time $t_e$ cannot be easily measured, TD1 can be empirically chosen to allow sufficient time to collect essentially all charge carriers generated by an X-ray photon but not too long to risk have another incident X-ray photon. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the X-ray photon, which relates to the energy of the X-ray photon. The controller 310 may be configured to determine the bin the energy of the X-ray photon falls in, based on the output of the ADC 306.

After TD1 expires or digitization by the ADC 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident X-ray photon. Implicitly, the rate of incident X-ray photons the system 121 can handle in the example of FIG. 11 is limited by 1/(TD1+RST). If the first voltage comparator 301 has been deactivated, the controller 310 can activate it at any time before RST expires. If the controller 310 has been deactivated, it may be activated before RST expires.

Because the detector 100 has many pixels 150 that may operate in parallel, the detector can handle much higher rate of incident X-ray photons. This is because the rate of incidence on a particular pixel 150 is 1/N of the rate of incidence on the entire array of pixels, where N is the number of pixels.

Figure 12:
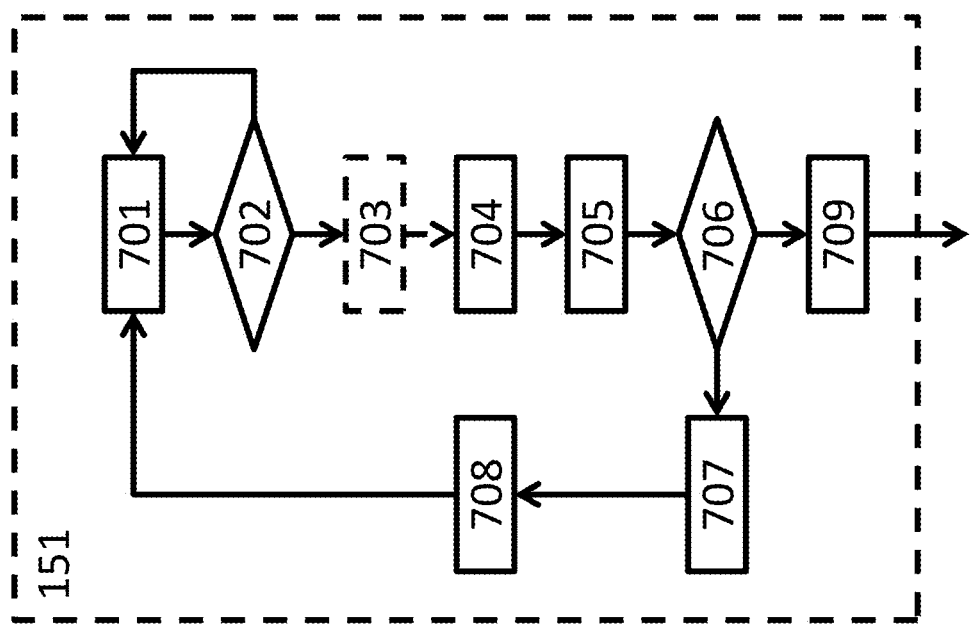
FIG. 12 shows an example flow chart for step 151 in FIG. 7, according to an embodiment.
Figure 13:
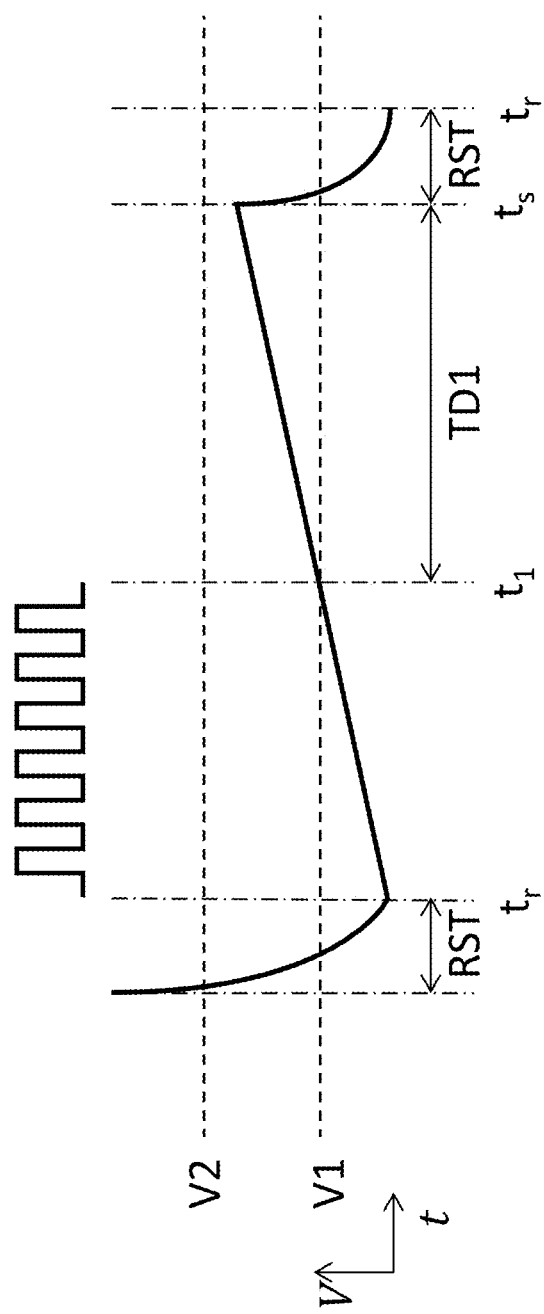
FIG. 13 schematically shows a temporal change of the voltage of the electric contact caused by the dark current, according to an embodiment.

FIG. 12 shows an example flow chart for step 151 in FIG. 8, according to an embodiment. In step 701, a voltage of an electric contact 119B of a diode or a resistor exposed to X-ray photons (e.g., fluorescent X-ray) is compared, e.g., using the first voltage comparator 301, to the first threshold. In step 702, it is determined whether the absolute value of the voltage equals or exceeds the absolute value of the first threshold V1, e.g., using the controller 310. If the absolute value of the voltage does not equal or exceed the absolute value of the first threshold, the method goes back to step 701. Namely, the voltage is monitored in step 701 and step 702 until the voltage reaches V1. If the absolute value of the voltage equals or exceeds the absolute value of the first threshold, the flow continues to step 703. In step 703, $T=(t_1-t_0)$ is measured. As explained with respect to FIG. 11, $t_0$ is the time when the X-ray photon hits the diode or the resistor, charge carriers start being generated in the pixel 150, electric current starts to flow through the electric contact 119B, and the absolute value of the voltage of the electric contact 119B starts to increase; $t_1$ is the time when the absolute value of the voltage equals or exceeds the absolute value of the first threshold V1. In step 704, the time delay TD1 is started, e.g., using the controller 310. In step 705, the voltage is compared, e.g., using the second voltage comparator 302, to the second threshold V2. In step 706, it is determined, e.g., using the controller 310, whether the absolute value of the voltage equals or exceeds the absolute value of the second threshold V2 during TD1. If the absolute value of the voltage does not equal or exceed the absolute value of the second threshold during TD1, the voltage is considered caused by dark current and the flow goes to step 707. In step 707, the contribution of the dark current to the voltage is measured based on T. In an example, it may be determined whether T is greater than the largest T previously measured ($T_{max}$). $T_{max}=0$ if T is not previously measured. If T is greater than $T_{max}$, replace the value of $T_{max}$ with the value of T. The contribution of the dark current to the voltage is at a rate of $V1/T_{max}$. If the dark current is measured as in this example, the contribution of the dark current to the voltage at a time $T_m$ is $((t_m-t_r) \cdot V1/T_{max})$, where $t_r$ is the end of the last reset period. $(t_m-t_r)$, like any time intervals in this disclosure, can be measured by counting pulses (e.g., counting clock cycles or clock pulses). $T_{max}$ may be reset to zero before each measurement with the detector 100. T may be measured by counting the number of pulses between $t_1$ and $t_0$, as schematically shown in FIG. 11 and FIG. 13. Another way to measure the contribution of the dark current to the voltage using T includes extracting a parameter of the distribution of T (e.g., the expected value of T ("$T_{expected}$")) and estimate the rate of the contribution of the dark current to the voltage as $V1/T_{expected}$. In step 708, the voltage is reset, e.g., by connecting the electric contact 119B to an electrical ground. If the absolute value of the voltage equals or exceeds the absolute value of the second threshold V2 during TD1, the flow continues to step 709. In step 709, the voltage is measured after it stabilizes, at time $t_m$, and a contribution from a dark current is subtracted from the measured voltage. Time $t_m$ can be any time after TD1 expires and before RST. The result is provided to ADC in step 152 in FIG. 8. The time when the reset period ends (e.g., the time when the electric contact 119B is disconnected from the electrical ground) is $t_r$.

FIG. 13 schematically shows a temporal change of the voltage of the electric contact 119B caused by the dark current, according to an embodiment. After RST, the voltage increase due to the dark current. The higher the dark current, the less time it takes for the voltage to reach V1 (namely shorter T). Therefore, T is a measure of the dark current. The dark current is unlikely large enough to cause the voltage to reach V2 during TD1 but current caused by an incident X-ray photon is probably large enough to do so. This difference may be used to identify the effect of the dark current. The flow in FIG. 13 may be carried out in each pixel 150 as the pixel 150 measures a series of incident X-ray photons, which will allow capturing the changes of the dark current (e.g., caused by changing environment such as temperature).

The semiconductor X-ray detector 100 may be used for phase-contrast X-ray imaging (PCI) (also known as phase-sensitive X-ray imaging). PCI encompasses techniques that form an image of an object at least partially using the phase shift (including the spatial distribution of the phase shift) of an X-ray beam caused by that object. One way to obtain the phase shift is transforming the phase into variations in intensity.

PCI can be combined with tomographic techniques to obtain the 3D-distribution of the real part of the refractive index of the object. PCI is more sensitive to density variations in the object than conventional intensity-based X-ray imaging (e.g., radiography). PCI is especially useful for imaging soft tissues.

Figure 14:
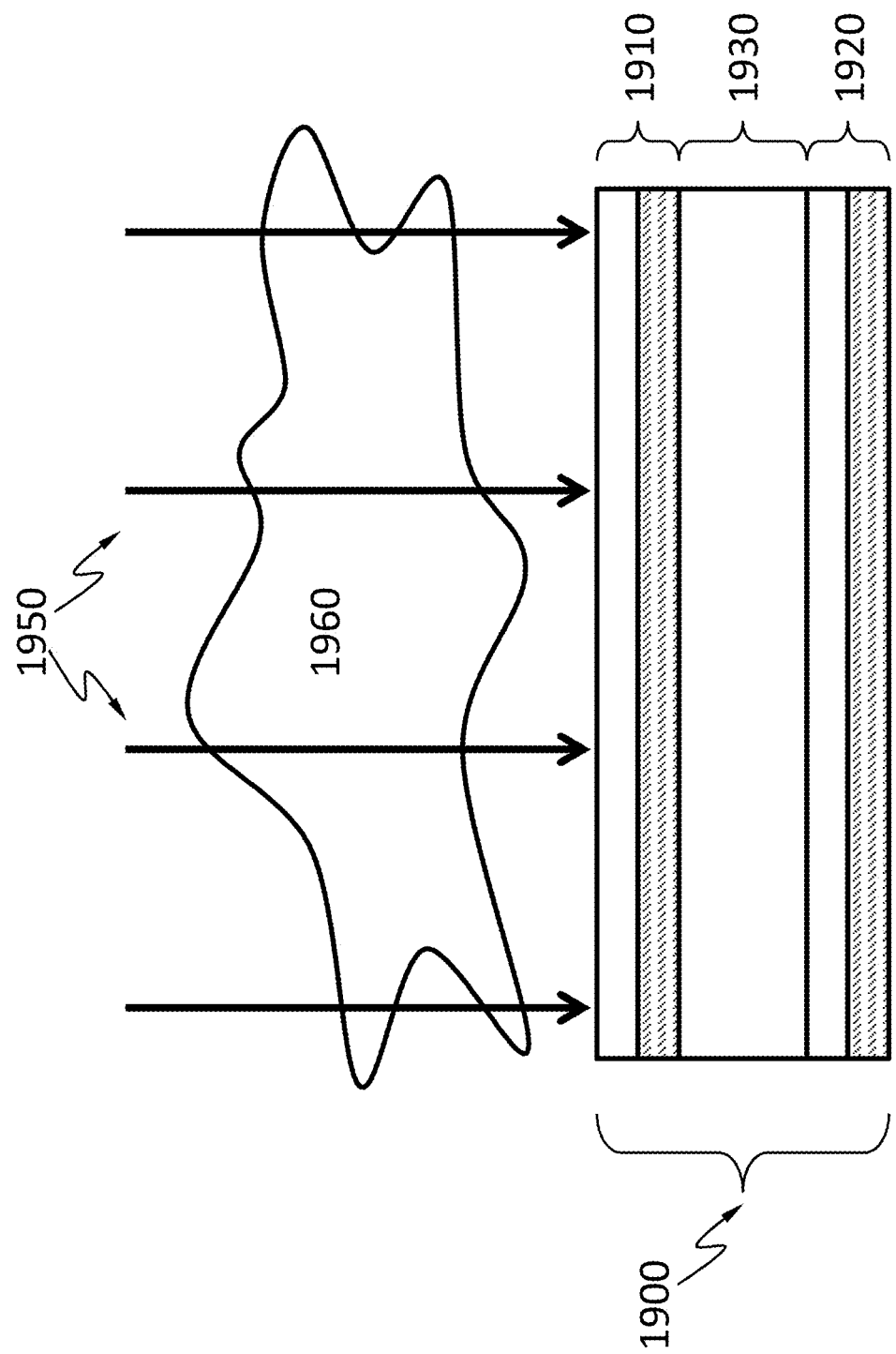
FIG. 14 schematically shows a system suitable for phase-contrast X-ray imaging (PCI), according to an embodiment.

According to an embodiment, FIG. 14 schematically shows a system 1900 suitable for PCI. The system 1900 may include at least two X-ray detectors 1910 and 1920. One or both of the two X-ray detectors 1910 and 1920 is the semiconductor X-ray detector 100 described herein. The X-ray detectors 1910 and 1920 may be spaced apart by a spacer 1930. The spacer 1930 may have very little absorption of the X-ray. For example, the spacer 1930 may have a very small mass attenuation coefficient (e.g., <10 cm$^2$g$^{-1}$, <1 cm$^2$g$^{-1}$, <0.1 cm$^2$g$^{-1}$, or <0.01 cm$^2$g$^{-1}$). The mass attenuation coefficient of the spacer 1930 may be uniform (e.g., variation between every two points in the spacer 1930 less than 5%, less than 1% or less than 0.1%). The spacer 1930 may cause the same amount of changes to the phase of X-ray passing through the spacer 1930. For example, the spacer 1930 may be a gas (e.g., air), a vacuum chamber, may comprise aluminum, beryllium, silicon, or a combination thereof.

The system 1900 can be used to obtain the phase shift of incident X-ray 1950 caused by an object 1960 being imaged. The incident X-ray 1950 may be generated by one or more of the X-ray sources 201 as described herein. The X-ray detectors 1910 and 1920 can capture two images (i.e., intensity distributions) simultaneously. Because of the X-ray detectors 1910 and 1920 are separated by the spacer 1930, the two images are different distances from the object 1960. The phase may be determined from the two images, for example, using algorithms based on the linearization of the Fresnel diffraction integral.

Figure 15:
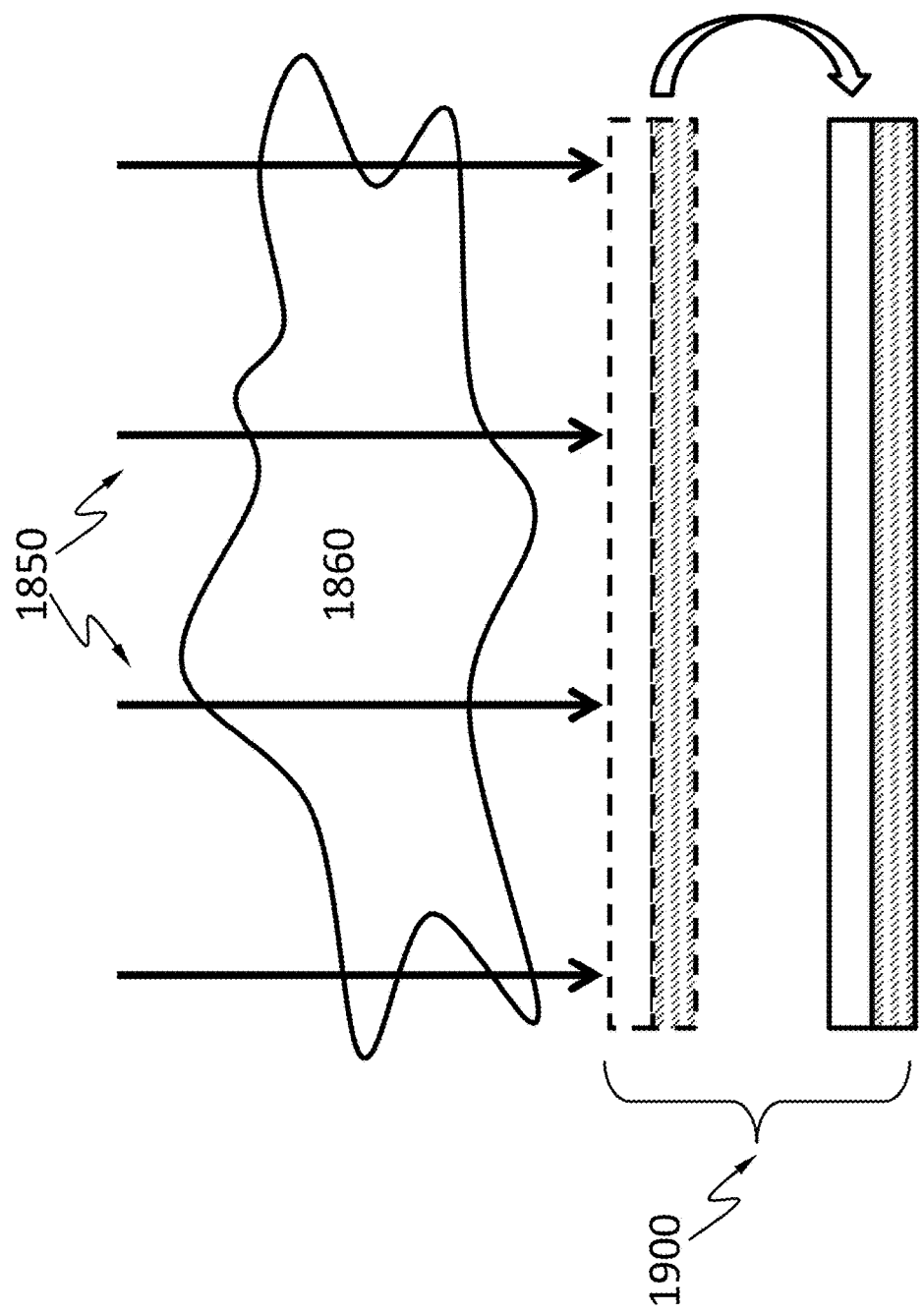
FIG. 15 schematically shows a system suitable for phase-contrast X-ray imaging (PCI), according to an embodiment.

According to an embodiment, FIG. 15 schematically shows a system 1800 suitable for PCI. The system 1800 comprises the semiconductor X-ray detector 100 described herein. The semiconductor X-ray detector 100 is configured to move to and capture images of an object 1860 exposed to incident X-ray 1850 at different distances from the object 1860. The incident X-ray 1850 may be generated by one or more of the X-ray sources 201 as described herein. The images may not necessarily be captured simultaneously. The phase may be determined from the images, for example, using algorithms based on the linearization of the Fresnel diffraction integral.

Figure 16:
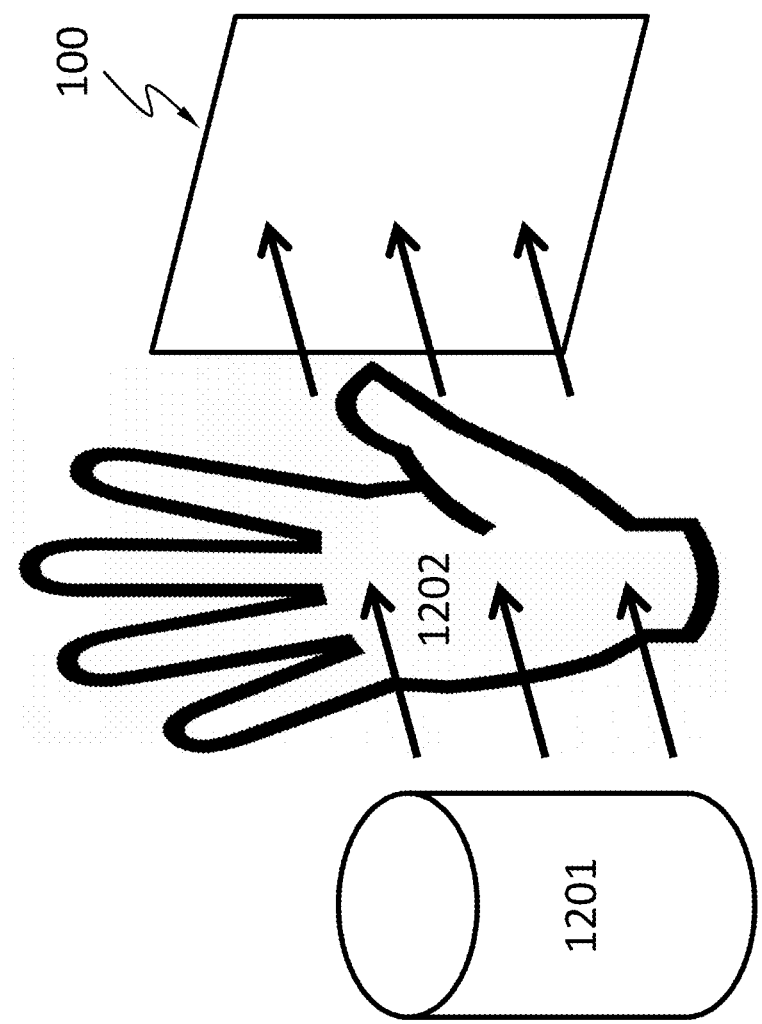
FIG. 16 schematically shows a system comprising the X-ray detector described herein, suitable for medical imaging such as chest X-ray radiography, abdominal X-ray radiography, etc., according to an embodiment.

FIG. 16 schematically shows a system comprising the semiconductor X-ray detector 100 described herein. The system may be used for medical imaging such as chest X-ray radiography, abdominal X-ray radiography, etc. The system comprises an X-ray source 1201, which may include one or more of the X-ray sources 201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the semiconductor X-ray detector 100. The semiconductor X-ray detector 100 forms an image by detecting the intensity distribution of the X-ray.

Figure 17:
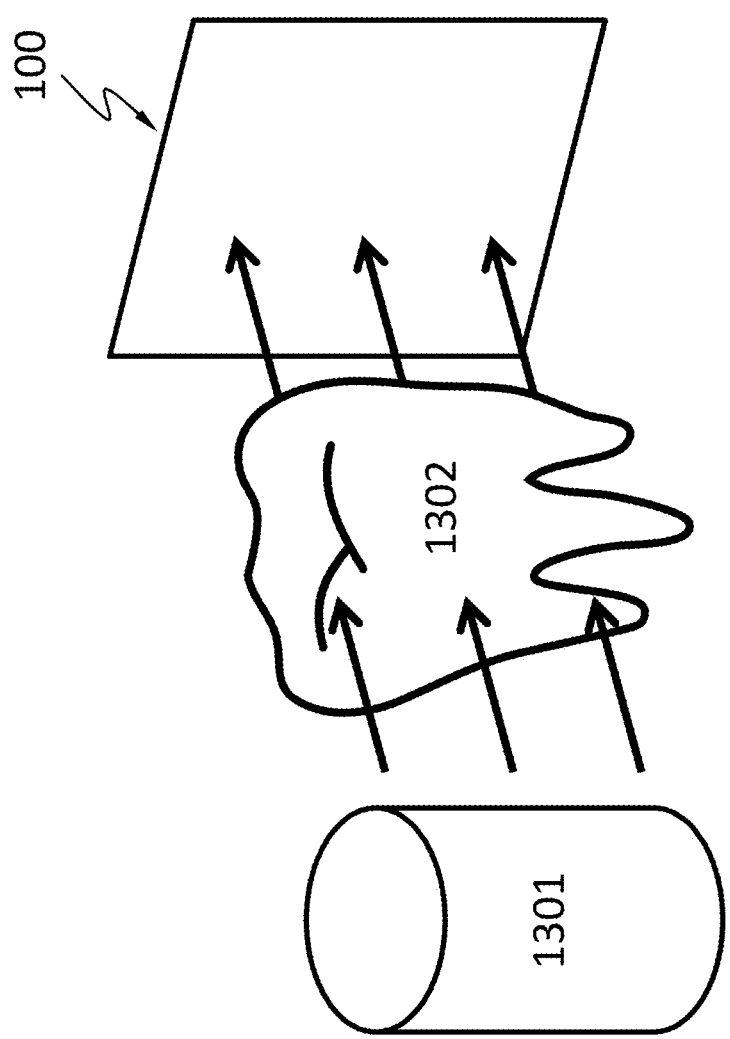
FIG. 17 schematically shows a system comprising the X-ray detector described herein suitable for dental X-ray radiography, according to an embodiment.

FIG. 17 schematically shows a system comprising the semiconductor X-ray detector 100 described herein. The system may be used for medical imaging such as dental X-ray radiography. The system comprises an X-ray source 1301, which may include one or more of the X-ray sources 201 as described herein. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the semiconductor X-ray detector 100. The semiconductor X-ray detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 18:
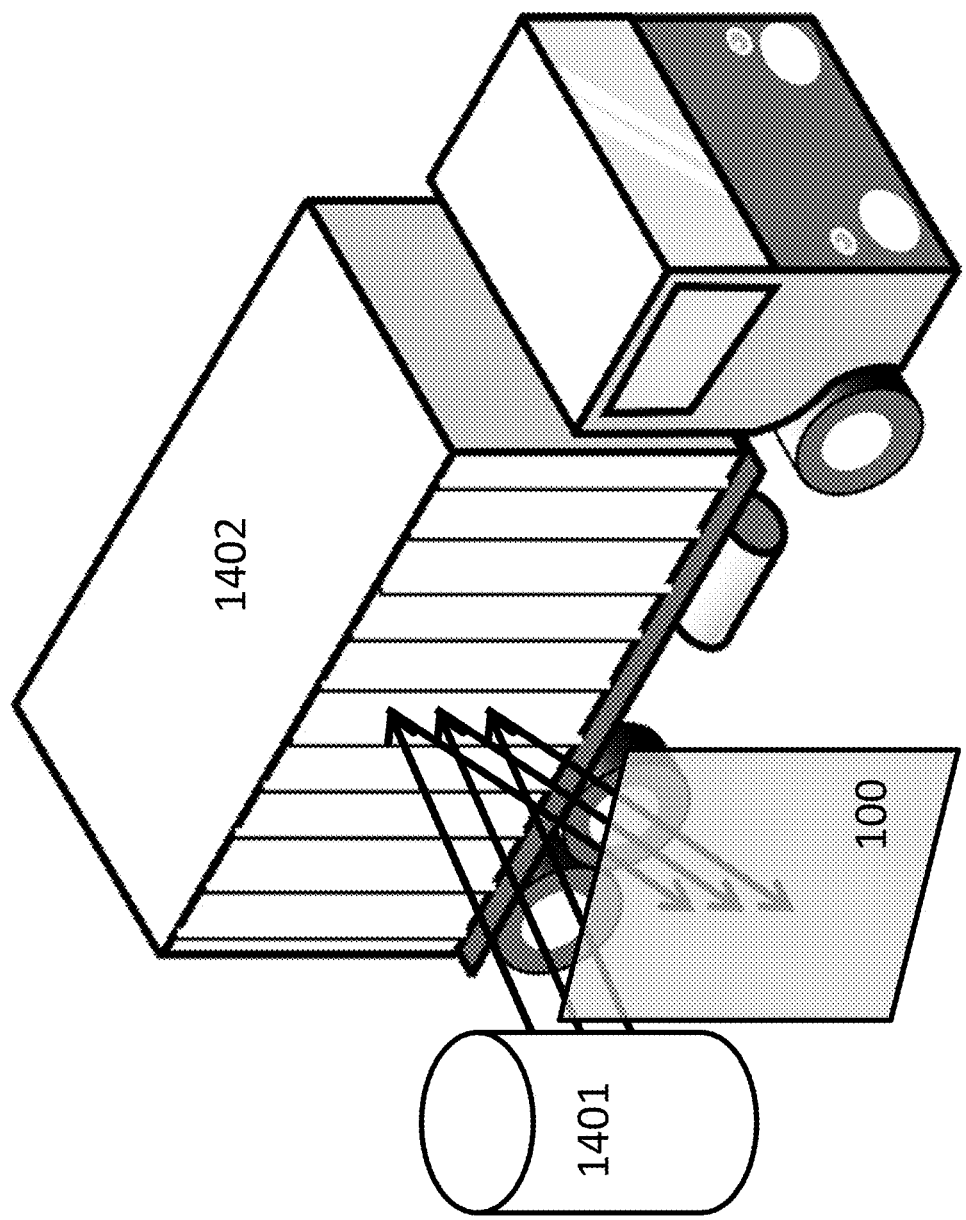
FIG. 18 schematically shows a cargo scanning or non-intrusive inspection (NII) system comprising the X-ray detector described herein, according to an embodiment.

FIG. 18 schematically shows a cargo scanning or non-intrusive inspection (NII) system comprising the semiconductor X-ray detector 100 described herein. The system may be used for inspecting and identifying goods in transportation systems such as shipping containers, vehicles, ships, luggage, etc. The system comprises an X-ray source 1401, which may include one or more of the X-ray sources 201. X-ray emitted from the X-ray source 1401 may backscatter from an object 1402 (e.g., shipping containers, vehicles, ships, etc.) and be projected to the semiconductor X-ray detector 100. Different internal structures of the object 1402 may backscatter X-ray differently. The semiconductor X-ray detector 100 forms an image by detecting the intensity distribution of the backscattered X-ray and/or energies of the backscattered X-ray photons.

Figure 19:
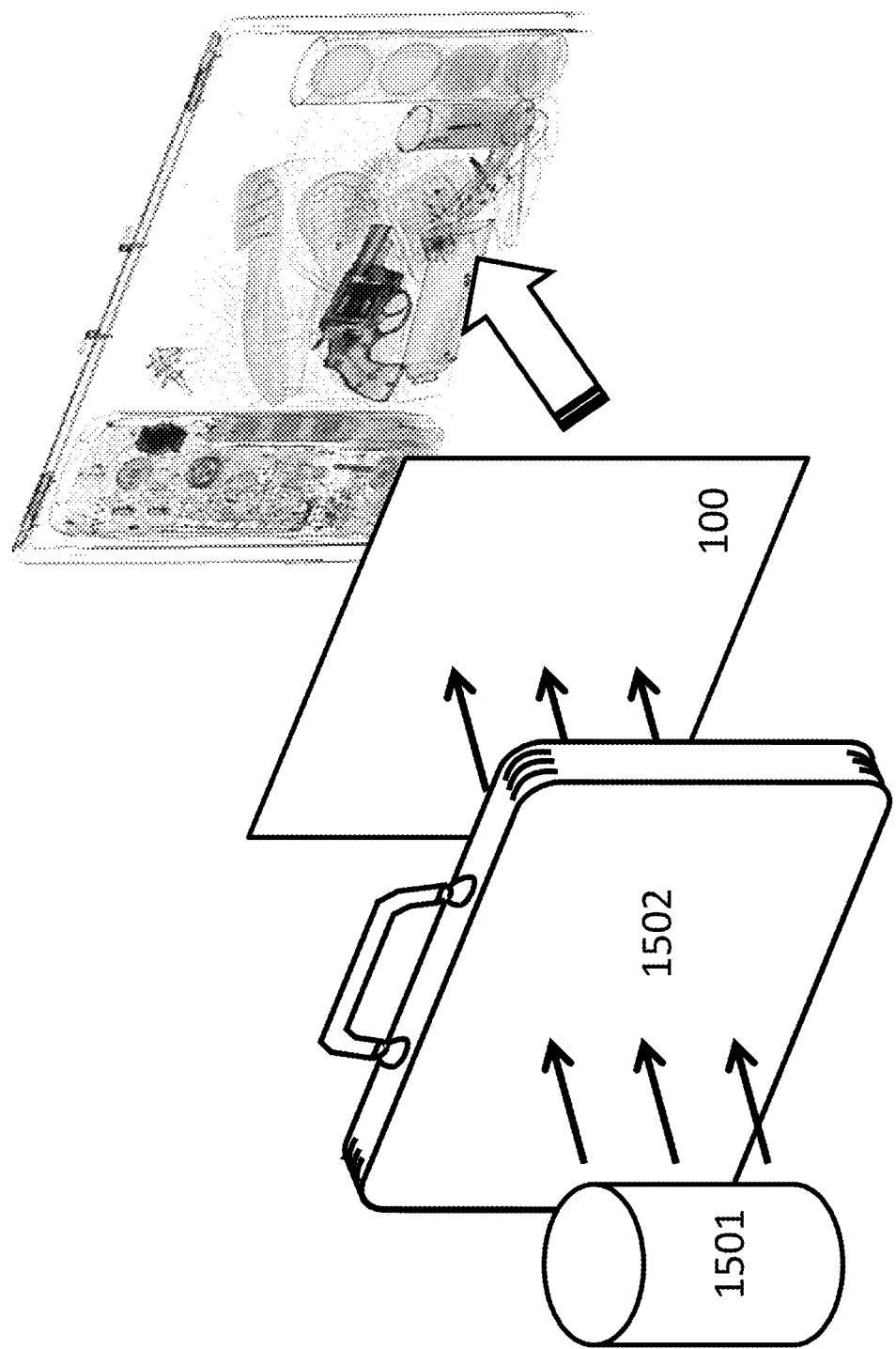
FIG. 19 schematically shows another cargo scanning or non-intrusive inspection (NII) system comprising the X-ray detector described herein, according to an embodiment.

FIG. 19 schematically shows another cargo scanning or non-intrusive inspection (NII) system comprising the semiconductor X-ray detector 100 described herein. The system may be used for luggage screening at public transportation stations and airports. The system comprises an X-ray source 1501, which may include one or more of the X-ray sources 201. X-ray emitted from the X-ray source 1501 may penetrate a piece of luggage 1502, be differently attenuated by the contents of the luggage, and projected to the semiconductor X-ray detector 100. The semiconductor X-ray detector 100 forms an image by detecting the intensity distribution of the transmitted X-ray. The system may reveal contents of luggage and identify items forbidden on public transportation, such as firearms, narcotics, edged weapons, flammables.

Figure 20:
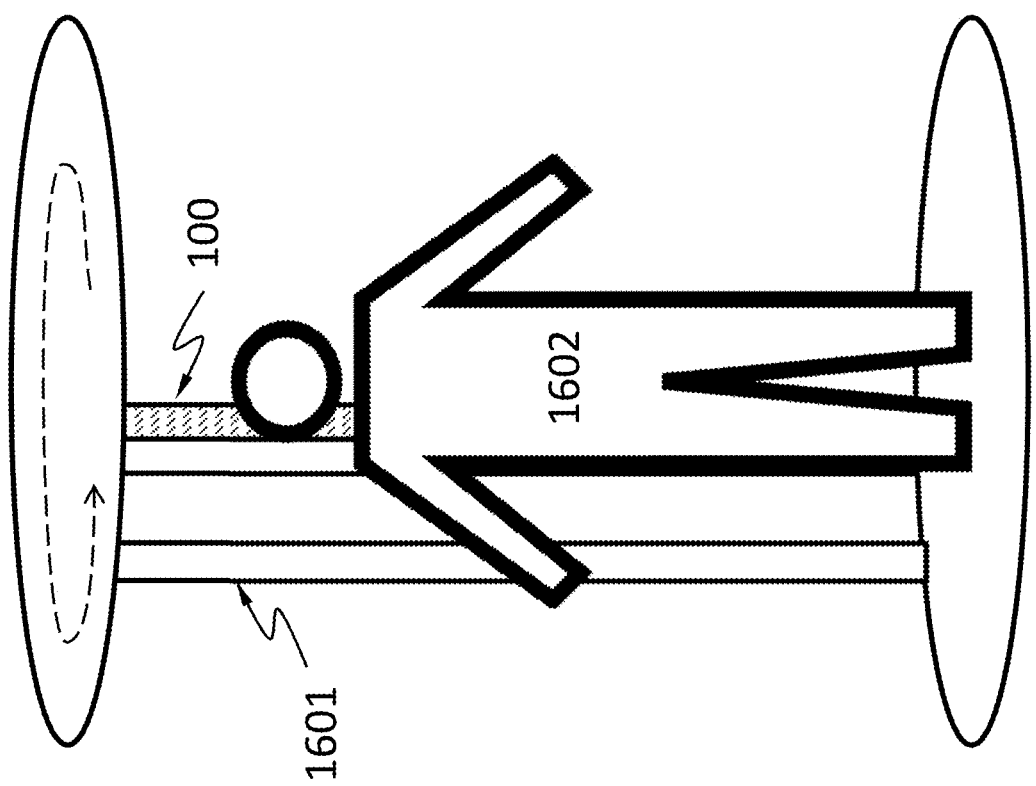
FIG. 20 schematically shows a full-body scanner system comprising the X-ray detector described herein, according to an embodiment.

FIG. 20 schematically shows a full-body scanner system comprising the semiconductor X-ray detector 100 described herein. The full-body scanner system may detect objects on a person's body for security screening purposes, without physically removing clothes or making physical contact. The full-body scanner system may be able to detect non-metal objects. The full-body scanner system comprises an X-ray source 1601, which may include one or more of the X-ray sources 201. X-ray emitted from the X-ray source 1601 may backscatter from a human 1602 being screened and objects thereon, and be projected to the semiconductor X-ray detector 100. The objects and the human body may backscatter X-ray differently. The semiconductor X-ray detector 100 forms an image by detecting the intensity distribution of the backscattered X-ray. The semiconductor X-ray detector 100 and the X-ray source 1601 may be configured to scan the human in a linear or rotational direction.

Figure 21:
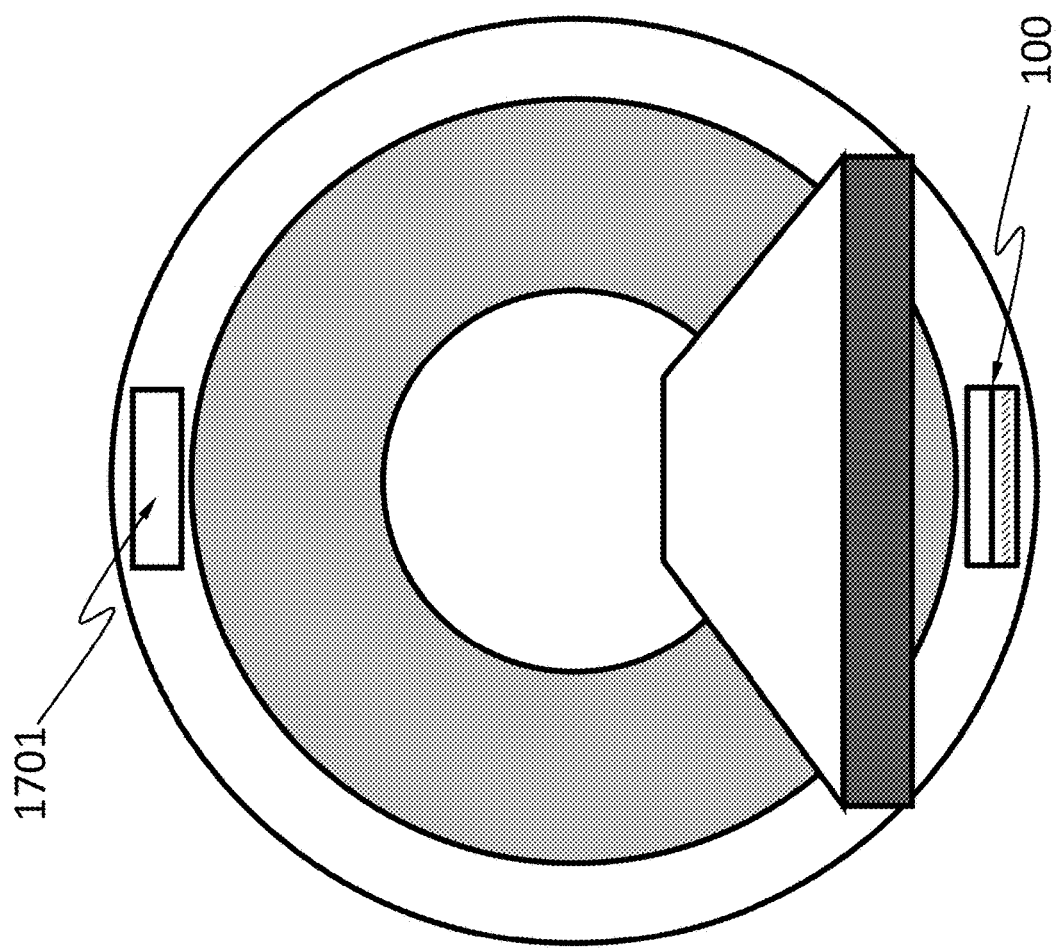
FIG. 21 schematically shows an X-ray computed tomography (X-ray CT) system comprising the X-ray detector described herein, according to an embodiment.

FIG. 21 schematically shows an X-ray computed tomography (X-ray CT) system comprising the semiconductor X-ray detector 100 described herein. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 100 described herein and an X-ray source 1701, which may include one or more of the X-ray sources 201. The semiconductor X-ray detector 100 and the X-ray source 1701 may be configured to rotate synchronously along one or more circular or spiral paths.

Figure 22:
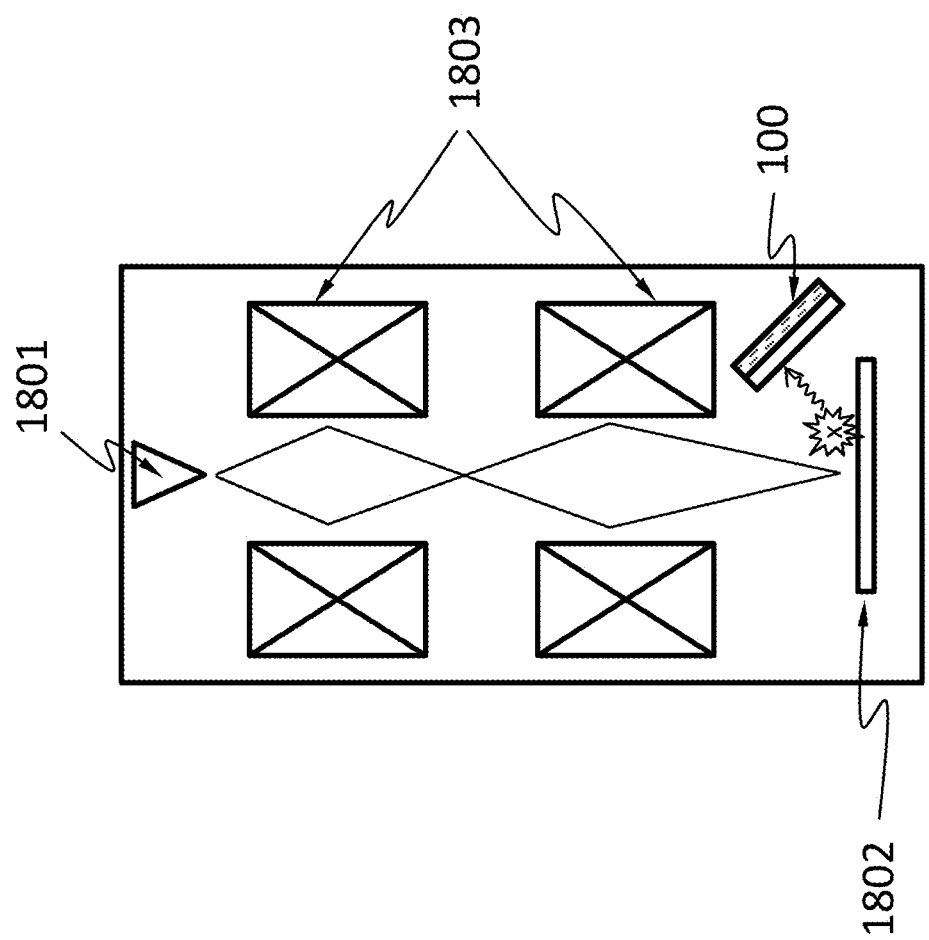
FIG. 22 schematically shows an electron microscope comprising the X-ray detector described herein, according to an embodiment.

FIG. 22 schematically shows an electron microscope comprising the semiconductor X-ray detector 100 described herein. The electron microscope comprises an electron source 1801 (also called an electron gun) that is configured to emit electrons. In an embodiment, the electron source 1801 may include one or more of the X-ray sources 201. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the semiconductor X-ray detector 100 described herein, for performing energy-dispersive X-ray spectroscopy (EDS). EDS is an analytical technique used for the elemental analysis or chemical characterization of a sample. When the electrons incident on a sample, characteristic X-rays may be emitted from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the semiconductor X-ray detector 100.

Figure 23:
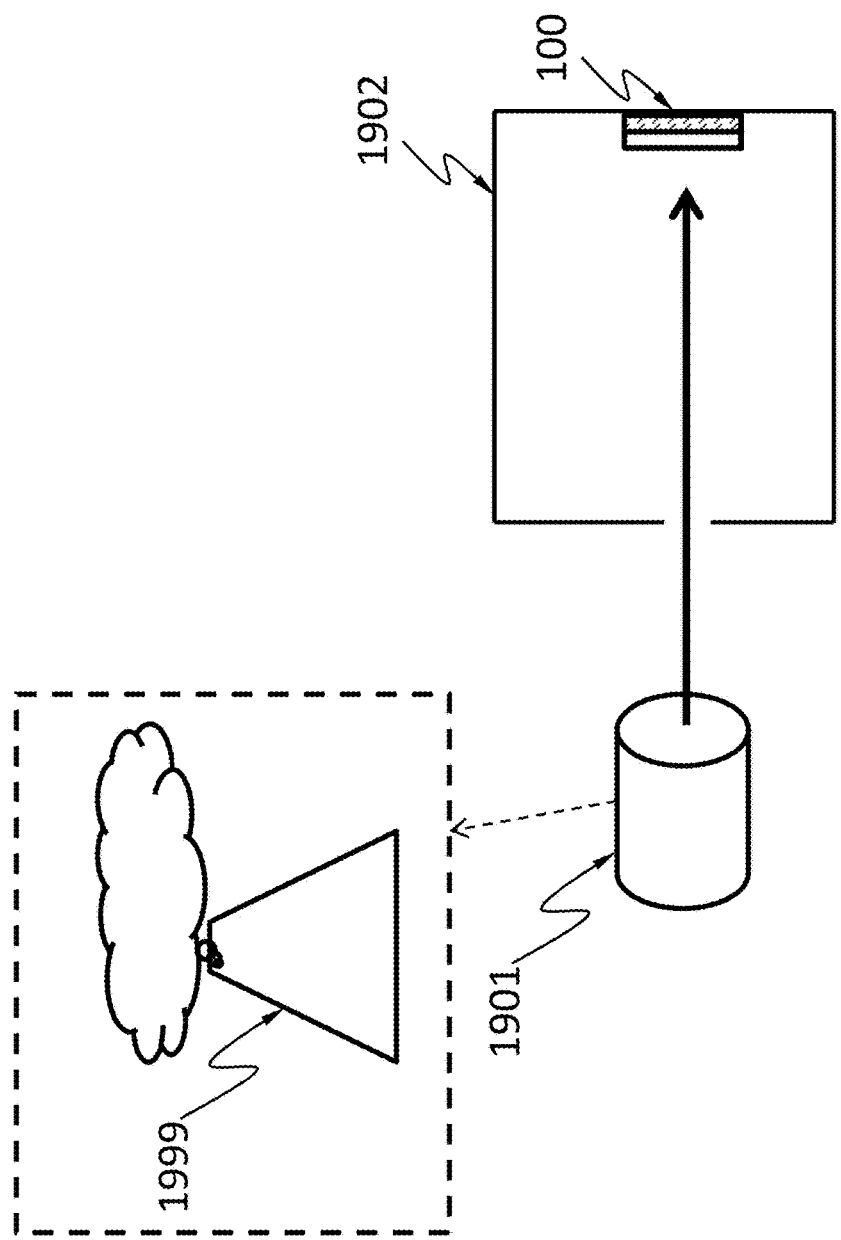
FIG. 23 schematically shows a radiation dose meter, according to an embodiment.

FIG. 23 schematically shows a radiation dose meter comprising the semiconductor X-ray detector 100 described herein. The radiation dose meter is capable of measuring an average dose rate of a radiation, e.g. X-ray, from a radiation source 1901. In an embodiment, the radiation source 1901 may include one or more of the X-ray sources 201. The radiation source 1901 may be a volcano 1999 or an atom bomb explosion. The radiation dose meter may include a chamber 1902 that includes air or other gas. X-ray going through a gas will ionize it, producing positive ions and free electrons. An incoming photon will create a number of such ion pairs proportional to its energy. An X-ray detector associated with the radiation dose meter can measure the average dose rate over the gas volume or the number of interacting photons.

Figure 24:
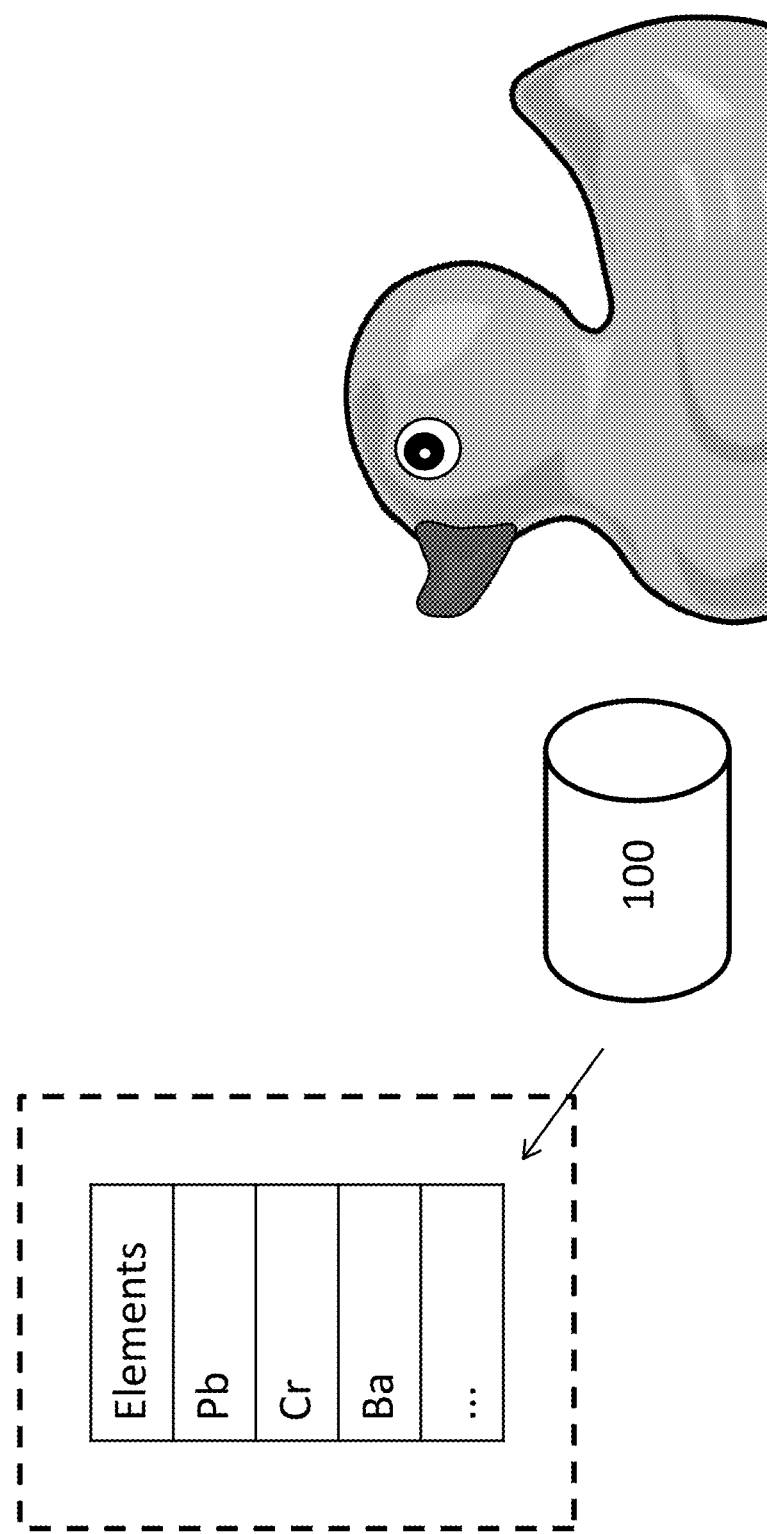
FIG. 24 schematically shows an element analyzer, according to an embodiment.

FIG. 24 schematically shows an element analyzer comprising the semiconductor X-ray detector 100 described herein. The element analyzer measurer is capable of detecting presence of one or more elements of interest on an object such as a toy. A high-energy beam of charged particles such as electrons or protons, or a beam of X-rays, is directed onto the object. In an embodiment, the high-energy beam, e.g., the beam of X-rays may be generated from the X-ray generator 299. Atoms of the objects are excited and emit X-ray at specific wavelengths that are characteristic of the elements. The X-ray detector 100 receives the emitted X-ray and determines the presence of the elements based on the energy of the emitted X-ray. For example, the X-ray detector 100 may be configured to detect X-ray at wavelengths Pb would emit. If the X-ray detector 100 actually receives X-ray from the object at these wavelengths, it can tell that Pb is present. The semiconductor X-ray detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this semiconductor X-ray detector 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An X-ray source, comprising:
a cathode in a recess of a first substrate;
a counter electrode on a sidewall of the recess, configured to cause field emission of electrons from the cathode;
a metal anode configured to receive the electrons emitted from the cathode and to emit X-ray from impact by the electrons on the metal anode; and
a shield electrode between the counter electrode and the metal anode, the shield electrode configured to prevent all of the electrons from reaching the metal anode.

2. The X-ray source of claim 1, wherein the cathode comprises a plurality of carbon nanotubes.

3. The X-ray source of claim 1, wherein the counter electrode is a continuous ring or dotted ring around the sidewall.

4. The X-ray source of claim 1, wherein the shield electrode is a continuous ring or dotted ring around the sidewall.

5. The X-ray source of claim 1, wherein the first substrate comprises silicon or silicon oxide.

6. The X-ray source of claim 1, wherein the metal anode comprises one or more metals selected from a group consisting of tungsten, molybdenum, rhenium, copper and combinations thereof.

7. The X-ray source of claim 1, further comprising a second substrate bonded to the first substrate, wherein the second substrate covers the recess.

8. The X-ray source of claim 7, wherein the metal anode is supported by the second substrate.

9. The X-ray source of claim 8, wherein the metal anode is on a side of the second substrate away from the cathode.

10. The X-ray source of claim 1, wherein the cathode comprises an array of carbon nanotubes.

11. A system comprising:
a plurality of X-ray sources of claim 1,
a plurality of X-ray detectors, wherein the X-ray sources and the X-ray detectors are arranged alternately;
an X-ray shield configured to prevent X-ray from the X-ray sources from directly reaching the X-ray detectors.

12. The system of claim 11, wherein the X-ray shield is a layer of material between the X-ray detectors and the X-ray sources.

13. The system of claim 12, wherein the layer of material comprises tungsten (W) or lead (Pb).

14. The system of claim 13, wherein the layer of material has a thickness of 1.5-2 mm.

15. A system comprising the X-ray source of claim 1 and an X-ray detector, wherein the system is configured for performing X-ray radiography on human chest or abdomen.

16. A system comprising the X-ray source of claim 1 and an X-ray detector, wherein the system is configured for performing X-ray radiography on human mouth.

17. A cargo scanning or non-intrusive inspection (NII) system, comprising the X-ray source of claim 1 and an X-ray detector, wherein the cargo scanning or non-intrusive inspection (NII) system is configured for forming an image based on backscattered X-ray.

18. A cargo scanning or non-intrusive inspection (NII) system, comprising the X-ray source of claim 1 and an X-ray detector, wherein the cargo scanning or non-intrusive inspection (NII) system is configured for forming an image based on X-ray transmitted through an object inspected.

19. A full-body scanner system comprising the X-ray source of claim 1 and an X-ray detector.

20. An X-ray computed tomography (CT) system comprising the X-ray source of claim 1 and an X-ray detector.

21. A system suitable for phase-contrast X-ray imaging (PCI), the system comprising the X-ray source of claim 1 and an X-ray detector.

22. An element analyzer comprising the X-ray source of claim 1.

23. A system suitable for detecting X-ray fluorescence (XRF), the system comprising the X-ray source of claim 1 and an X-ray detector.

24. The X-ray source of claim 1, wherein the shield electrode is configured to prevent the electrons from reaching the metal anode by repelling the electrons away from the metal anode.

25. The X-ray source of claim 1, wherein the shield electrode is electrically insulated from the counter electrode.

26. The X-ray source of claim 1, wherein the shield electrode is not exposed in the recess.

* * * * *